(12) United States Patent
Russell et al.

(10) Patent No.: US 9,307,925 B2
(45) Date of Patent: Apr. 12, 2016

(54) METHODS AND SYSTEMS FOR GENERATING ELECTRICAL PROPERTY MAPS OF BIOLOGICAL STRUCTURES

(75) Inventors: Michael J. Russell, Davis, CA (US); David F. Wiley, Woodland, CA (US)

(73) Assignee: Aaken Laboratories, Davis, CA (US)

( * ) Notice: Subject to any disclaimer, the term of this patent is extended or adjusted under 35 U.S.C. 154(b) by 86 days.

(21) Appl. No.: 13/112,934

(22) Filed: May 20, 2011

(65) Prior Publication Data

US 2011/0288400 A1 Nov. 24, 2011

Related U.S. Application Data

(63) Continuation-in-part of application No. 11/424,813, filed on Jun. 16, 2006, now abandoned.

(60) Provisional application No. 60/691,068, filed on Jun. 16, 2005.

(51) Int. Cl.
  *A61B 5/055* (2006.01)
  *A61B 5/00* (2006.01)
  *A61B 6/00* (2006.01)
  *A61N 1/36* (2006.01)
  *A61B 6/03* (2006.01)

(52) U.S. Cl.
  CPC .............. *A61B 5/055* (2013.01); *A61B 5/0035* (2013.01); *A61B 5/0042* (2013.01); *A61B 5/4058* (2013.01); *A61B 5/4064* (2013.01); *A61B 6/5247* (2013.01); *A61N 1/36067* (2013.01); *A61B 5/004* (2013.01); *A61B 5/40* (2013.01); *A61B 6/032* (2013.01); *A61N 1/3605* (2013.01); *A61N 1/3606* (2013.01); *A61N 1/36014* (2013.01); *A61N 1/36017* (2013.01); *A61N 1/36025* (2013.01); *A61N 1/36082* (2013.01)

(58) Field of Classification Search
  USPC ......................................... 600/410, 411, 416
  See application file for complete search history.

(56) References Cited

U.S. PATENT DOCUMENTS

| | | |
|---|---|---|
| 3,786,391 A | 1/1974 | Mathauser |
| 3,865,099 A | 2/1975 | Robichaud |
| 3,964,470 A | 6/1976 | Trombley |
| 4,306,564 A | 12/1981 | Kraus |
| 4,421,115 A | 12/1983 | Kraus |
| 4,569,351 A | 2/1986 | Tang |
| 4,611,597 A | 9/1986 | Kraus |
| 5,255,692 A | 10/1993 | Neubauer et al. |
| 5,701,895 A | 12/1997 | Prutchi et al. |
| 5,725,377 A | 3/1998 | Lemler et al. |

(Continued)

OTHER PUBLICATIONS

Functional Magnetic Resonance Imaging (fMRI), by Robert L. Savoy; Encyclopedia of the Brain: May 2003.*

(Continued)

*Primary Examiner* — Katherine Fernandez
*Assistant Examiner* — Michael Kellogg
(74) *Attorney, Agent, or Firm* — Kunzler Law Group

(57) ABSTRACT

A method performed at a computer system having one or more processors and memory storing one or more programs for execution by the one or more processors is disclosed. The method includes accessing multiple images of a biological structure, generating an electrical property map of at least a portion of the biological structure in accordance with two or more of the multiple images, and providing at least a subset of the electrical property map.

20 Claims, 20 Drawing Sheets
(7 of 20 Drawing Sheet(s) Filed in Color)

(56) References Cited

U.S. PATENT DOCUMENTS

| | | | |
|---|---|---|---|
| 5,750,895 A | 5/1998 | Chern et al. | |
| 5,805,267 A | 9/1998 | Goldman | |
| 5,964,794 A | 10/1999 | Bolz et al. | |
| 5,995,651 A | 11/1999 | Gelenbe et al. | |
| 5,995,863 A | 11/1999 | Farace et al. | |
| 6,006,124 A | 12/1999 | Fischell et al. | |
| 6,045,532 A | 4/2000 | Eggers et al. | |
| 6,052,608 A | 4/2000 | Young et al. | |
| 6,106,466 A | 8/2000 | Sheehan et al. | |
| 6,175,769 B1 | 1/2001 | Errico et al. | |
| 6,230,049 B1 | 5/2001 | Fischell et al. | |
| 6,236,738 B1 | 5/2001 | Zhu et al. | |
| 6,248,080 B1 | 6/2001 | Miesel et al. | |
| 6,319,241 B1 | 11/2001 | King et al. | |
| 6,322,549 B1 | 11/2001 | Eggers et al. | |
| 6,324,433 B1 | 11/2001 | Errico | |
| 6,330,446 B1 | 12/2001 | Mori | |
| 6,397,095 B1* | 5/2002 | Eyuboglu et al. | 600/411 |
| 6,463,317 B1 | 10/2002 | Kucharczyk et al. | |
| 6,476,804 B1 | 11/2002 | Costabel | |
| 6,560,487 B1 | 5/2003 | McGraw et al. | |
| 6,594,521 B2* | 7/2003 | Tucker | 600/544 |
| 6,607,500 B2 | 8/2003 | Da Silva et al. | |
| 6,608,628 B1 | 8/2003 | Ross et al. | |
| 6,662,035 B2 | 12/2003 | Sochor | |
| 6,675,048 B2 | 1/2004 | McGraw et al. | |
| 6,763,140 B1 | 7/2004 | Skoll | |
| 6,795,737 B2 | 9/2004 | Gielen et al. | |
| 6,919,294 B2 | 7/2005 | Saito et al. | |
| 6,937,905 B2 | 8/2005 | Carroll et al. | |
| 6,959,215 B2 | 10/2005 | Gliner et al. | |
| 7,010,351 B2 | 3/2006 | Firlik et al. | |
| 7,079,977 B2 | 7/2006 | Osorio et al. | |
| 7,107,104 B2 | 9/2006 | Keravel et al. | |
| 7,221,981 B2 | 5/2007 | Gliner | |
| 7,263,401 B2 | 8/2007 | Scott et al. | |
| 7,302,298 B2 | 11/2007 | Lowry et al. | |
| 7,346,382 B2 | 3/2008 | McIntyre et al. | |
| 7,514,921 B2* | 4/2009 | Woo et al. | 324/300 |
| 7,620,456 B2 | 11/2009 | Gliner et al. | |
| 7,795,870 B2* | 9/2010 | Sodickson et al. | 324/309 |
| 2002/0156372 A1 | 10/2002 | Skakoon et al. | |
| 2003/0023159 A1 | 1/2003 | Tanner | |
| 2004/0073270 A1 | 4/2004 | Firlik et al. | |
| 2004/0102828 A1 | 5/2004 | Lowry et al. | |
| 2004/0215162 A1 | 10/2004 | Putz | |
| 2005/0003268 A1 | 1/2005 | Scott et al. | |
| 2005/0021019 A1* | 1/2005 | Hashimshony et al. | 606/32 |
| 2005/0065427 A1* | 3/2005 | Magill et al. | 600/407 |
| 2005/0075680 A1 | 4/2005 | Lowry et al. | |
| 2005/0131506 A1 | 6/2005 | Rezai et al. | |
| 2005/0177039 A1 | 8/2005 | Mills et al. | |
| 2005/0244036 A1 | 11/2005 | Rusinek et al. | |
| 2005/0245984 A1 | 11/2005 | Singhal et al. | |
| 2005/0246002 A1 | 11/2005 | Martinez | |
| 2005/0283203 A1 | 12/2005 | Flaherty et al. | |
| 2006/0017749 A1* | 1/2006 | McIntyre et al. | 345/664 |
| 2006/0129203 A1 | 6/2006 | Garabedian et al. | |
| 2006/0173493 A1 | 8/2006 | Armstrong et al. | |
| 2006/0173522 A1 | 8/2006 | Osorio | |
| 2006/0241374 A1 | 10/2006 | George et al. | |
| 2007/0043268 A1 | 2/2007 | Russell | |
| 2007/0053554 A1* | 3/2007 | Fayad et al. | 382/128 |
| 2007/0106143 A1 | 5/2007 | Flaherty | |
| 2007/0123954 A1 | 5/2007 | Gielen et al. | |
| 2008/0300652 A1 | 12/2008 | Lim et al. | |
| 2010/0036453 A1 | 2/2010 | Hulvershorn et al. | |
| 2010/0113959 A1 | 5/2010 | Pascual-Leone et al. | |
| 2010/0283484 A1 | 11/2010 | Cohen et al. | |

OTHER PUBLICATIONS

Brain Tumor Localization Using an Electrical Impedance Technique by L. W. Organ et al., J Neurosurg. Jan. 1968;28(1):35-44.*

Display of Merged Multimodality Brain Images Using Interleaved Pixels with Independent Color Scales by Kelly Rehm et al. J Nucl Med 1994; 35:1815-1821.*

Q-Ball Imaging by David S. Tuch, pub. Magnetic Resonance in Medicine 52:1358-1372 (2004).*

Volumetric Transformation of Brain Anatomy by Christensen et al. pub. IEEE Transactions on Medical Imaging, vol. 16, No. 6, Dec. 1997.*

Amassian, Animal and Human Motor System Neurophysiology Related to Intraoperative Monitoring, Neurophysiology in Neurosurgery: A Modern Intraoperative Approach, 2002, pp. 3-23.

Ary, Location of Sources of Evoked Scalp Potentials: Corrections for Skull and Scalp Thicknesses, Biomedical Engineering, vol. BME-28, No. 6, Jun. 1981, pp. 447-452.

Benar, Modeling of Post-Surgical Brain and Skull Defects in the EEG Inverse Problem with the Boundary Element Method, Clinical Neurophysiology 113, 2002, pp. 48-56.

Ben-David, Anterior Spinal Fusion Complicated by Paraplegia: A Case Report of a False-negative Somatosensory-evoked Potential, Anterior Fusion and Paraplegia, Spine, vol. 12, No. 6, pp. 536-539.

Berry, Nervous System, Grey's Anatomy, 1995, pp. 1186-1195.

Bose, Neurophysiological monitoring of spinal cord function during instrumented anterior cervical fusion, The Spine Journal 4, 2004, pp. 202-207.

Butson, Patient-specific analysis of the volume of tissue activated during deep brain stimulation, NeuroImage 34, 2007, pp. 661-670.

Calancie, Threshold-level repetitive transcranial electrical stimulation for intraoperative monitoring of central motor conduction, J Neurosurg Spine 1 95, 2001, pp. 161-168.

Cheney, Patterns of Facilitation and Suppression of Antagonist Forelimb Muscles from Motor Cortex Sites in the Awake Monkey, Journal of Neurophysiology vol. 53, No. 3, Mar. 1985, pp. 805-820.

Chiappa, Transcranial motor evoked potentials, Electromyogr.clin. Neurophysiol., 1994, pp. 15-21.

Deletis, Intraoperative Neurophysiology and Methodologies Used to Monitor the Functional Integrity of the Motor System, Neurophysiology in Neurosurgery: A Modern Intraoperative Approach, 2002, pp. 25-51.

Eroglu, Stress Hormones During the Wake-up Test in Scoliosis Surgery, Journal of Clinical Anesthesia, 2003, pp. 15-18.

Ferree, Regional Head Tissue Conductivity Estimation for Improved EEG Analysis, IEEE Transactions of Biomedical Engineering, vol. 47, No. 12, Dec. 2000, pp. 1584-1592.

Geddes, The Specific Resistance of Biological Material—A Compendium of Data for the Biomedical Engineer and Physiologist, Med. & biol. Engng. vol. 5, 1967, pp. 271-293.

Ginsburg, Postoperative paraplegia with preserved intraoperative somatosensory evoked potentials, J. Neurosug., vol. 63, Aug. 1985, pp. 296-300.

Goncalves, In vivo Measurement of the Brain and Skull Resistivities using an EIT-Based Method and the Combined Analysis of SEF/SEP Data, IEE Transaction on Biomedical Engineering, vol. 50, No. 9, Sep. 2003, pp. 1124-1128.

Grimnes, Bioimpedance and Bioelectricity Basics, 2000.

Haghighi, Activation of the External Anal and Urethral Sphincter Muscles by Repetitive Transcranial Cortical Stimulation During Spine Surgery, Journal of Clinical Monitoring and Computing, vol. 18, 2004, pp. 1-5.

Haueisen, Influence of Tissue Resistivities on Neuromagnetic Fields and Electric Potentials Studied with a Finite Element Model of the Head, IEEE Transactions on Biomedical Engineering, vol. 44, No. 8, Aug. 1997, pp. 727-735.

Henderson, The Localization of the Equivalent Dipoles of EEG Sources by the Application of Electric Field Theory, 1975, pp. 117-130.

Kavanagh, Evaluation of Methods for the Three-Dimensional Localization of Electrical Sources in the Human Brain, IEE Transactions of Biomedical Engineering, vol. BME-25, No. 5, Sep. 1978, pp. 421-429.

Kirson, Alternating electric fields arrest cell proliferation in animal tumor models and human brain tumors, PNAS, vol. 104, No. 24, Jun. 12, 2007, pp. 10152-10157.

Law, Thickness and Resistivity Variations over the Upper Surface of the Human Skull, Brain Topography, vol. 6, No. 2, 1993, pp. 99-109.

(56) References Cited

OTHER PUBLICATIONS

Lesser, Postoperative Neurological Deficits May Occur Despite Unchanged Intraoperative Somotosensory Evoked Potentials, 1986, pp. 22-25.

Liu, Effects of isolurane and propofol on cortical somatosensory evoked potentials during comparable depth of anaesthesia as guided by bispectral index, British Journal of Anaesthesia, 94, 2, 2005, pp. 193-197.

MacDonald, Monitoring Scoliosis Surgery with Combined Multiple Pulse Transcranial Electric Motor and Cortical Somatosensory-Evoked Potentials from the Lower and Upper Extremities, Spine vol. 28, No. 2, 2003, pp. 194-203.

Mustain, Dissociation of Neurogenic Motor and Somatosensory Evoked Potentials: A Case Report, 1991, pp. 851-853.

Nadeem, Computation of Electric and Magnetic Stimualtion in Human Head Using the 3-D Impedance Method, IEEE Transactions on Biomedical Engineering, vol. 50, No. 7, 2003, pp. 900-907.

Oostendorp, The Conductivity of the Human Skull: Results of In Vivo and In Vitro Measurements, IEE Transactions on Biomedical Engineering, vol. 47, No. 11, Dec. 2000, pp. 1487-1492.

Pelosi, Combined monitoring of motor and somatosensory evoked potentials in orthopaedic spinal surgery, Clinical Neurophysiology 113, 2002, pp. 1082-1091.

Rush, Current Distribution in the Brain From Surface Electrodes, Anesthesia and Analgesia, vol. 47, No. 6, Nov.-Dec. 1968, pp. 717-723.

Russell, International Preliminary Report on Patentability, PCT/US2006/023751, Mar. 17, 2009, 6 pgs.

Russell, International Search Report and Written Opinion, PCT/US2006/023751, Jun. 12, 2008, 6 pgs.

Russell, Notice of Allowance, U.S. Appl. No. 12/139,443, Aug. 19, 2011, 8 pgs.

Russell, Office Action, AU 2006261150, Dec. 3, 2010, 2 pgs.

Russell, Office Action, CN 200680028116.X, Jan. 19, 2011, 2 pgs.

Russell, Office Action, U.S. Appl. No. 11/424,813, Feb. 15, 2011, 13 pgs.

Russell, Office Action, U.S. Appl. No. 12/139,443, Dec. 20, 2010, 12 pgs.

Schneider, Effect of Inhomogeneities on Surface Signals Coming from a Cerebral Current-Dipole Source, IEE Transactions of Biomedical Engineering, Jan. 1974, pp. 52-54.

Sersa, Electrochemotherapy of Mouse Sarcoma Tumors Using Electric Pulse Trains with Repetition Frequencies of 1 Hz and 5 kHz, J Membrane Biol, 2010, pp. 155-162.

Sharan, MR safety in patients with implanted deep brain stimulation systems (DBS), 2003, pp. 141-145.

Tang, Correlation Between Structure and Resistivity Variations of the Live Human Skull, IEEE Transactions on Biomedical Engineering, vol. 55, No. 9, Sep. 2008, pp. 2286-2292.

Trost, Comprehensive short-term outcome assessment of selective dorsal rhizotomy, Developmental Medicine & Child Neurology, 2008, pp. 765-771.

Ubags, The Use of a Circumferential Cathode Improves Amplitude of Intraoperative Electrical Transcranial Myogenis Motor Evoked Responses, 1996, pp. 1011-1014.

Vauzelle, Functional Monitoring of Spinal Cord Activity During Spinal Surgery, Clinical Orthopaedic and Related Research, No. 93, Jun. 1973, pp. 173-178.

Zentner, Noninvasive Motor Evoked Potential Monitoring During Neurosurgical Operations on the Spinal Cord, Neurosurgery, vol. 24, No. 5, 1989, pp. 709-712.

Zhang, Electrically Guiding Migration of Human Induced Pluripotent Stem Cells, Stem Cell Rev and Rep, 2011, pp. 987-996.

* cited by examiner

1300

1302 Access multiple images of a biological structure

1304 The multiple images of the biological structure include two or more of: T1, T2, and proton density MRI images; a magnetic resonance angiography image; and an X-ray computed-tomography image

1306 The multiple images of the biological structure include T1, T2, and proton density MRI images

1308 Generate an electrical property map of at least a portion of the biological structure in accordance with two or more of the multiple images

1310 Generating the electrical property map includes: generating a combined image of T1, T2, and proton density MRI images of the biological structure; and determining respective electrical property values for respective regions of the combined image

1312 Generating the electrical property map includes: generating a combined image of at least the portion of the biological structure; and determining respective electrical property values for respective regions of the combined image.

1314 Each image of the biological structure includes a plurality of respective regions. Each region has multiple bits. Generating the combined image includes, for each region corresponding to at least the portion of the biological structure, interleaving at least a subset of the multiple bits from respective images.

1316 The respective electrical property values include respective tissue resistivity values. Determine respective tissue resistivity values in accordance with an equation:

$$R(v) = K(1-v)^E + D$$

1318 Determine respective conductivity values for respective regions of the combined image

1320 Generating the electrical property map includes: generating a weighted-sum image of the two or more of the multiple images

Figure 13A

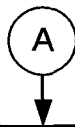

1322  Provide at least a subset of the electrical property map

1324  The multiple images include a functional MRI image.
Overlay at least a subset of the functional MRI image onto the electrical property map of at least the portion of the biological structure.

1326  Identify one or more electrode sites for providing stimulation of at least a respective region of the biological tissue in accordance with at least the subset of the electrical property map 1328  Identify one or more inductance sites for providing magnetic pulse stimulation of at least a respective region of the biological tissue in accordance with at least the subset of the electrical property map

1502 Receive an electrical property map corresponding to at least a portion of the biological structure. The electrical property map is generated in accordance with multiple images of the biological structure.

1504 Place one or more electrodes at one or more sites on the biological structure corresponding to one or more electrode sites identified in accordance with at least a subset of the electrical property map

| 1506 Identify one or more respective locations of the tumor cells in the biological structure. Identify the one or more electrode sites in accordance with the one or more respective locations of the tumor cells in the biological structure and at least the subset of the electrical property map. |

1508 Apply applying one or more electric inputs using the one or more electrodes for killing the cells in the biological structure

Figure 15

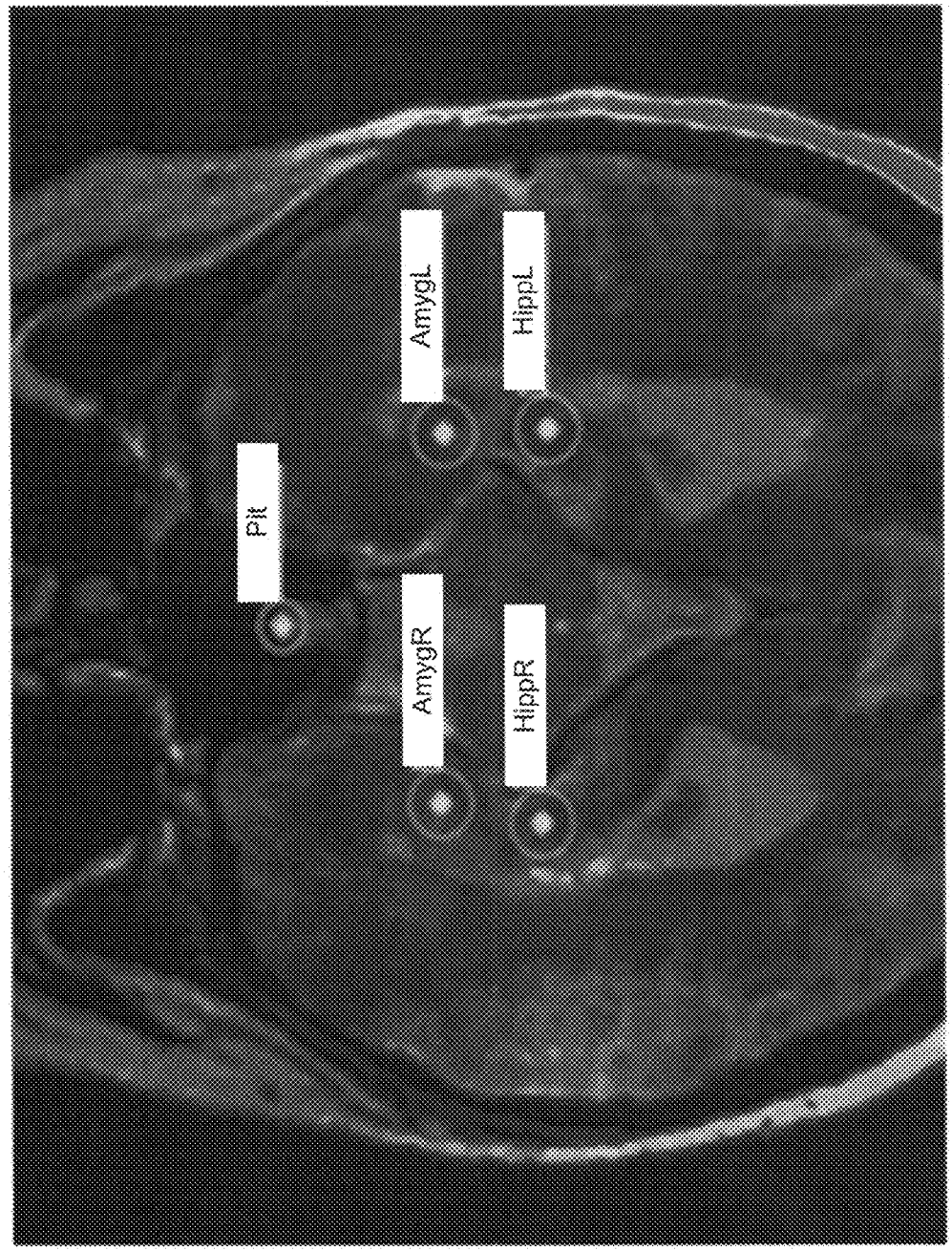

METHODS AND SYSTEMS FOR GENERATING ELECTRICAL PROPERTY MAPS OF BIOLOGICAL STRUCTURES

RELATED APPLICATIONS

This application is a continuation-in-part of U.S. patent application Ser. No. 11/424,813, filed Jun. 16, 2006 now abandoned, which claims the benefit of priority to U.S. Provisional Patent Application Ser. No. 60/691,068, filed Jun. 16, 2005, both of which are incorporated by reference herein in their entirety.

BACKGROUND

1. Field of the Invention

The invention relates to combining multiple images of a biological structure, particularly to determining electrical properties (e.g., resistivities and/or conductivities) of the biological structure from multiple images of the biological structure.

2. Description of the Related Art

The advent of transcranially stimulated electrical motor evoked potentials (tcMEPs) has resulted in a dramatic reduction in the rate of paralysis for high risk surgical patients (see Chappa K H, 1994, Calanchie et al 2001, Pelosi et al. 2002, Bose B, Sestokas A K, Swartz D M 2004 and MacDonald et al 2003, citations below and hereby incorporated by reference). As a consequence tcMEPs have become the standard of care for testing the integrity of the cortical spinal track during spinal and neurosurgical procedures. Unfortunately, transcranial electrical stimulation has generally required high voltages with diffuse current spread that causes the activation of large regions of the brain and puts the patient at risk of unwanted and unknown side effects. Obtaining more precisely directed current at lower voltages will reduce the risk and greatly expand the utility of transcranial stimulation for surgical and non-surgical patents.

It is desired to have a technique involving site specific transcranial electrical stimulation of the brain that approximates physiological current densities, and to apply these techniques to treat expanded patient populations, including spinal surgery patients. Transcranial electrical stimulation to elicit motor evoked potentials (tcMEPs) has become the standard of care for monitoring the motor pathways of the spinal cord and brain during high risk surgeries. A conventional tcMEP technique can often be a crude, but effective tool to monitor motor pathways and to identify iatrogenic injuries. FIG. 1A illustrates a tcMEP from a scoliosis patient. The scale of FIG. 1A shows 50 µV on the y-axis and 7.5 ms on the x-axis. Applied pulses were 150 Volts for 100 µs in trains of five pulses with an inter stimulus interval (ISI) of 3 ms. FIG. 1B illustrates a tcMEP from a 86 year old male with a neck fracture. Applied pulses were 75 Volts in the upper plot and 25 Volts in the lower plot.

Typically, a tcMEPs procedure involves placing electrodes in the patient's scalp at locations that are thought to encompass the motor cortex and then applying brief high voltage electrical pulses with the intention of activating distal muscles or muscle groups. FIG. 2 illustrates placement of electrodes $J_0$ outside of a patient's scalp. FIG. 2 also illustrates three regions $S_0$, $S_1$, and $S_2$ having different conductivities $\sigma_1$, $\sigma_2$, and $\sigma_3$, respectively. Unfortunately, the high voltages typically used to induce tcMEPs and the responses they produce can activate whole regions of the head, body, or trunk as well as the target muscles. The movement of large muscle groups due to the uncontrolled current spread means that seizures, broken jaws and patient movement create risk factors that have been associated with tcMEP testing (see Chappa, K H, 1994, citation below). Applying stimulus trains rather than single pulses and adjustments in anesthesia techniques have significantly reduced the applied electrical currents used from 700-900 V to 200-400 V (see Chappa, K H.1994, Haghighi S S, and Zhange R 2004, citations below and hereby incorporated by reference).

TcMEPs have become widely accepted as a less onerous substitute for "wake-up tests" in which the patient is awakened during surgery and asked to move their limbs before the surgical procedure is completed (see Eroglu, A et al. 2003, citation below and hereby incorporated by reference). However, these reduced stimulus levels still exceed normal physiological levels and the uncontrolled movement of large muscle groups suggests that the applied pulses continue to result in significant current spreads. While major side effects are relatively rare, tongue lacerations, muscle tears, and bucking are still rather common side effects (see Calanchie, B et al. 2001, citation below and hereby incorporated by reference). The large muscle movements that are sometimes associated with tcMEPs also limit the usefulness of the tcMEPs during periods when the surgeon is involved in delicate brain or spinal procedures.

It is desired to reduce or eliminate these side effects by predicting the paths of electrical pulses within the brain and consequently adjusting current levels (i.e., lower). It is also desired to reduce the current strength to near physiological levels at targeted areas to allow brain electrical stimulation to be used for treatment of patients outside of surgery. In this way, a significant positive impact on the treatment of a number of disease conditions that have been demonstrated to benefit from brain electrical stimulation, e.g., Parkinson's disease, chronic pain, and depression, can be achieved.

Modeling

The head is a heterogeneous, anisotropic conductive medium with multiple conductive compartments. Finding the current path through this medium has been a significant problem in neurophysiology. For decades it has been the dream of many investigators to stimulate the brain through this medium without the use of brain surgery or depth electrodes. It is desired to provide an innovative solution to this problem.

There is a volume of literature attempting to model current pathways and tissue resistivity that was developed for understanding the source generators of electroencephalography (EEG) (see Rush S, Driscoll D A 1968, Vauzelle, C., Stagnara 1973; Henderson, C J, Butler, S R, and Class A, 1978; Benar & Gotman, 2002; Henderson et al., 1975; and Kavanagh et al., 1978, citations below and hereby incorporated by reference).

Several authors have attempted to construct such physical models of the head. Some of these physical models were made of plastic, saline and/or silicon. They are not sufficient to represent the complexity of the problem and do not account for individuals' anatomical differences.

Finite element (FE) forward modeling has benefited from recent improvements in estimates of skull and tissue resistivity. These newer estimates were obtained in vivo (see Goncalves et al., 2003; and Oostendorp et al., 2000, citations below and hereby incorporated by reference). These provide more precise values of indigenous tissues than many of the previous estimates that were typically done on dried or cadaver tissues.

Several groups have attempted to resolve the problem of transcranial stimulation by using commercially available transcranial magnetic stimulators. Although magnetic stimulators are commonly used in clinics, they have been rejected for surgical applications because of the difficulty in using them in an environment with multiple metal objects and their tendency for the stimulation parameters to be less consistent than those produced by electrical stimulation. Small movements of the magnetic pulse generators have resulted in significant changes in the stimulus parameters and the coil cannot be used for chronic conditions wherein treatment would involve continuous stimulation. It is desired to accurately model head tissues and current pathways to more efficiently target cerebral activation of corticospinal tract neurons by transcranial electrical stimulation.

SUMMARY OF THE INVENTION

A technique is provided for generating an electrical property map of a biological structure. MRI or CAT scan data, or both, are obtained for a biological structure (e.g., a subject's brain and/or another body tissue). Such electrical property map, if generated from multiple images of a brain, can be used for transcranial or intracranial application of electrical energy for monitoring or therapeutic purposes. In some embodiments, different anisotropic electrical values are assigned to portions of the subject brain or other body tissue. Electrode sites can be selected based on the electrical property map. In some embodiments, based on the electrical property map, one or more applied electrical voltages, powers, energies, currents or charges are calculated for application of transcranial or intracranial current, or trans-tissue current for other body tissues. The subject brain is an exemplary organ with which embodiments may be advantageously applied, but it is understood that the invention may be applied to other body parts or tissues besides the subject brain. It will also be understood that it is not intended to limit the invention to particular embodiments described herein. On the contrary, the invention is intended to cover alternatives, modifications and equivalents that are within the spirit and scope of the invention as defined by the appended claims.

In accordance with some embodiments, the method includes segmenting the subject brain by defining tissue compartment boundaries between, and assigning one or more electrical characteristics to, said portions of the subject brain, implementing a finite element model by defining a mesh of grid elements for the subject brain, and ascribing vector resistance values to each of the grid elements based on the segmenting. The segmenting may include discriminating two or more of cerebrospinal fluid, white matter, blood, skin, gray matter, soft tissue, cancellous bone, eye fluid, cancerous tissue, inflammatory tissue, ischemic tissue, and compact bone. The discriminating may involve resolving peaks in a histogram for a combined image generated with multiple images of the subject brain.

As used herein, the term "electrical value" and/or "electrical property" refers to one of: conductivity, resistivity, capacitance, impedance, polarity, and applied energy, or a combination thereof "Electrical characteristics" may include characteristics relating to conductivities, resistivities, capacitances, impedances, or applied energies, or combinations thereof "Resistance values" may include resistivities or conductivities or both. The data may include a combination of two or more types of MRI or CAT scan data, or both, such as two or more of T1, T2 and PD MRI data. The data typically includes three-dimensional data.

In accordance with some embodiments, the method includes disposing the electrodes on the surface of the skin, in or below the skin (subdermal), or within the skull tissue, and in alternative embodiments, disposing the electrodes through the skull proximate to or in contact with the dura, or at a shallow transdural location. In the alternative embodiments, the method includes utilizing a screw mounted electrode within or through the skull tissue. In some embodiments, the method includes disposing the electrodes deep within a tissue.

A further technique is provided for determining an optimal transcranial or intracranial application of electrical energy for monitoring or therapeutic purposes. A combination of two or more types of three-dimensional MRI or CAT scan data, or both, is obtained for a subject brain. Different electrical values are assigned to portions of the subject brain based on the data. In this embodiment, electrode sites are selected including disposing at least one electrode at least partially through the skull. Based on the assigning and selecting, one or more applied electrical inputs, such as voltage, energy, power, charge, or electrical pulses or pulses trains of selected duration, height, or number, or combinations thereof, are calculated for optimal therapeutic application of transcranial or intracranial electricity, typically in the form of current.

In accordance with some embodiments, the method includes defining tissue compartment boundaries between, and assigning one or more isotropic electrical resistance characteristics to, said portions of the subject brain or body tissue, implementing a finite element model by defining a mesh of grid elements for the subject brain or body tissue, and ascribing vector resistance values to each of the grid elements based on the segmenting. The segmenting may include discriminating two or more of cerebrospinal fluid, white matter, blood, skin, gray matter, soft tissue, cancellous bone, eye fluid, cancerous tissue, inflammatory tissue, ischemic tissue, and compact bone.

The data may include a combination of two of more of T1, T2 and PD MRI data. The method may include disposing at least one electrode through the skull proximate to or in contact with the dura, or in a shallow transdural location. The method may involve utilizing a screw mounted electrode within or through the skull tissue.

A further technique is provided for determining an optimal transcranial or intracranial application of electrical energy for monitoring or therapeutic purposes. MRI or CAT scan data, or both, are obtained for a subject brain and/or other body tissue. The subject brain or other body tissue is segmented by defining tissue compartment boundaries between, and assigning one or more electrical characteristics to, said portions of the subject brain of other body tissue. A finite element model is implemented by defining a mesh of grid elements for the subject brain or other body tissue. Electrical values are ascribed to each of the grid elements based on the segmenting. Electrode sites are selected. Based on the assigning and selecting, one or more applied electrical inputs, such as voltage, energy, power, charge, or electrical pulses or pulses trains of selected duration, height, or number, or combinations thereof, are calculated for optimal therapeutic application of transcranial or intracranial electricity, typically in the form of current.

In accordance with some embodiments, the electrical values include vector resistance values and the electrical characteristics may include anisotropies.

The segmenting may include discriminating two or more of cerebrospinal fluid, white matter, blood, skin, gray matter, soft tissue, cancellous bone, eye fluid, cancerous tissue, inflammatory tissue, ischemic tissue, and compact bone. The ascribing may include inferring anisotropies for the resistance values of the grid elements. The data may include a combination of two or more types of MRI or CAT scan data, or both, such as a combination of two of more of T1, T2 and PD MRI data. The data may include three-dimensional data.

A method is further provided for determining an optimal application of electrical energy for monitoring or therapeutic treatment based on MRI or CAT scan data, or both, of a subject brain and/or other body tissue, and different anisotropic electrical values assigned to portions of the subject brain or body tissue based on the data. The method involves selecting electrode sites, and calculating, based on the assigned anisotropic electrical values and the selecting, one or more applied electrical inputs, such as voltage, energy, power, charge, or electrical pulses or pulses trains of selected duration, height, or number, or combinations thereof for optimal therapeutic application of electricity, typically in the form of current.

The anisotropic values are typically assigned based on segmenting the subject brain by defining tissue compartment boundaries between, and one or more electrical characteristics to, said portions of the subject brain and/or other body tissue, implementing a finite element model by defining a mesh of grid elements for the subject brain, and ascribing vector electrical values to each of the grid elements based on the segmenting. The segmenting may involve discriminating two or more of cerebrospinal fluid, white matter, blood, skin, gray matter, soft tissue, cancellous bone, eye fluid, cancerous tissue, inflammatory tissue, ischemic tissue, and compact bone. The discriminating may involve resolving peaks within respective gray scale data corresponding to two or more brain or other body tissues.

A further method is provided for determining an optimal application of electrical energy for therapeutic treatment based on obtaining MRI or CAT scan data, or both, of a subject brain and/or other body tissue, and electrical values ascribed to grid elements of a mesh defined by implementing a finite element model for a subject brain and/or other body tissue, and by segmenting the subject brain and/or other body tissue by defining tissue compartment boundaries between, and one or more electrical characteristics to, said portions of the subject brain and/or other body tissue, and by implementing a finite element model by defining a mesh of grid elements for the subject brain and/or other body tissue, and ascribing electrical values to each of the grid elements based on the segmenting. The method includes selecting electrode sites, and calculating, based on the ascribed electrical values and selecting, one or more applied electrical inputs, such as voltage, energy, power, charge, or electrical pulses or pulses trains of selected duration, height, or number, or combinations thereof for optimal therapeutic application of transcranial or intracranial electricity, typically in the form of current.

The electrical values may be as defined above, and may include vector resistance values, while the electrical characteristics may be as defined above, and may include anisotropies. The segmenting may include discriminating two or more of cerebrospinal fluid, white matter, blood, skin, gray matter, soft tissue, cancellous bone, eye fluid, and compact bone. The ascribing may include inferring anisotropies for the resistance values of the grid elements.

One or more processor readable storage devices are also provided having processor readable code embodied thereon. The processor readable code is for programming one or more processors to perform any of the methods recited or described herein for determining an optimal application of electrical energy for therapeutic treatment.

In accordance with some embodiments, a method is performed at a computer system with one or more processors and memory storing one or more programs for execution by the one or more processors. The method includes: accessing multiple images of a biological structure, generating an electrical property map of at least a portion of the biological structure in accordance with two or more of the multiple images, and providing at least a subset of the electrical property map.

In accordance with some embodiments, a computer system includes one or more processors and memory storing one or more programs for execution by the one or more processors. The one or more programs include instructions for: accessing multiple images of a biological structure, generating an electrical property map of at least a portion of the biological structure in accordance with two or more of the multiple images, and providing at least a subset of the electrical property map.

In accordance with some embodiments, a non-transitory computer readable storage medium includes one or more programs for execution by one or more processors of a computer system. The one or more programs include instructions for: accessing multiple images of a biological structure, generating an electrical property map of at least a portion of the biological structure in accordance with two or more of the multiple images, and providing at least a subset of the electrical property map.

In accordance with some embodiments, a method for providing electrical or magnetic stimulation of a biological structure includes receiving an electrical property map corresponding to at least a portion of the biological structure. The electrical property map is generated in accordance with multiple images of the biological structure. The method includes placing one or more electrodes at one or more sites on the subject corresponding to one or more electrode sites identified in accordance with at least a subset of the electrical property map, and applying one or more electric or magnetic inputs using the one or more electrodes.

In accordance with some embodiments, a method of killing cells includes receiving an electrical property map corresponding to at least a portion of a biological structure. The electrical property map is generated in accordance with multiple images of the biological structure. The method includes placing one or more electrodes at one or more sites on the subject corresponding to one or more electrode sites identified in accordance with at least a subset of the electrical property map, and applying one or more electric inputs using the one or more electrodes for killing the cells in the biological structure.

In accordance with some embodiments, a method is performed at a computer system with one or more processors and memory storing one or more programs for execution by the one or more processors. The method includes receiving a combined image. The combined image includes a plurality of regions, each region having an intensity value, and the intensity value of each region is determined in accordance with intensity values of corresponding regions of multiple images of the biological structure. The method includes classifying tissues in at least a portion of the biological structure in accordance with the one or more intensity values in at least a subset of the combined image corresponding to at least the portion of the biological structure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 13A and 13B are flow diagrams illustrating a method for generating an electrical property map in accordance with some embodiments.

FIG. 15 is a flow diagram illustrating a method for killing cells in accordance with some embodiments.

FIGS. 17A and 17B illustrate current densities simulated based on MRI images of two individuals in accordance with some embodiments.

DETAILED DESCRIPTION OF THE EMBODIMENTS

Abbreviations

CT=X-ray Computed Tomography
GETs=Guided Electrical Transcranial stimulation
EEG=Electroencephalogram
MRI=Magnetic Resonance Imaging
T1 MRI=$T_1$-weighted MRI
T2 MRI=$T_2$-weighted MRI
PD MRI=Proton density weighted MRI (also known as spin density weighted MRI)
FE=Finite Element method
SEP=Somatosensory Evoked Potentials
fMRI=functional Magnetic Resonance Imaging
tcMEP=transcranial Motor Evoked Potentials

Introduction

As will be described in more detail below, solutions to the forward problem are achievable with matrix algebra by constructing a model of sufficient detail representing all the heterogeneities found within an individual's head and brain. The approach described below in the Detailed Description section has bypassed the use of a physical model and uses an individual's MRI and/or CT scan as a representation of the head and brain. MRI images and CT scans are digitized images that can be manipulated through computer programs to which standard algebraic manipulations can be applied. This digital modeling also allows the use of matrix algebra solutions that have been developed for other complex representations e.g. weather systems, fluid streams, etc. Further, modules within finite element (FE) analysis packages have been developed to represent time dependent factors such as capacitance and resistance.

It is further described below to advantageously reduce current densities by utilizing a three-dimensional (3-D) modeling of the head. Our pilot work has demonstrated that a two-dimensional (2-D) Guided Electrical Transcranial stimulation (GETs) developed in our laboratory is able to reduce current densities by 60 percent or more. Greater reduction is achieved with the 3-D model.

Effective embodiments are provided including combining CT scans with MRI images. Such combinations can be advantageously utilized as a base for a GETs model. Computed Tomography (CT) is a particularly effective method of imaging various biological structures and is utilized in some embodiments for further enhancing the GETs model.

In one embodiment, direct measurements are obtained of current within subject brains. In another embodiment, motor evoked potentials are obtained as a biological assay. A technique in accordance with exemplary embodiments works advantageously in reducing electrical current densities even when brain anatomy has been significantly altered by an injury, tumor, or developmental disorder.

In addition, GETs modeling can be applied to actual spinal surgery patients. This can serve to optimize transcranial stimulation of the motor cortex.

Preliminary Studies

Figure 3:
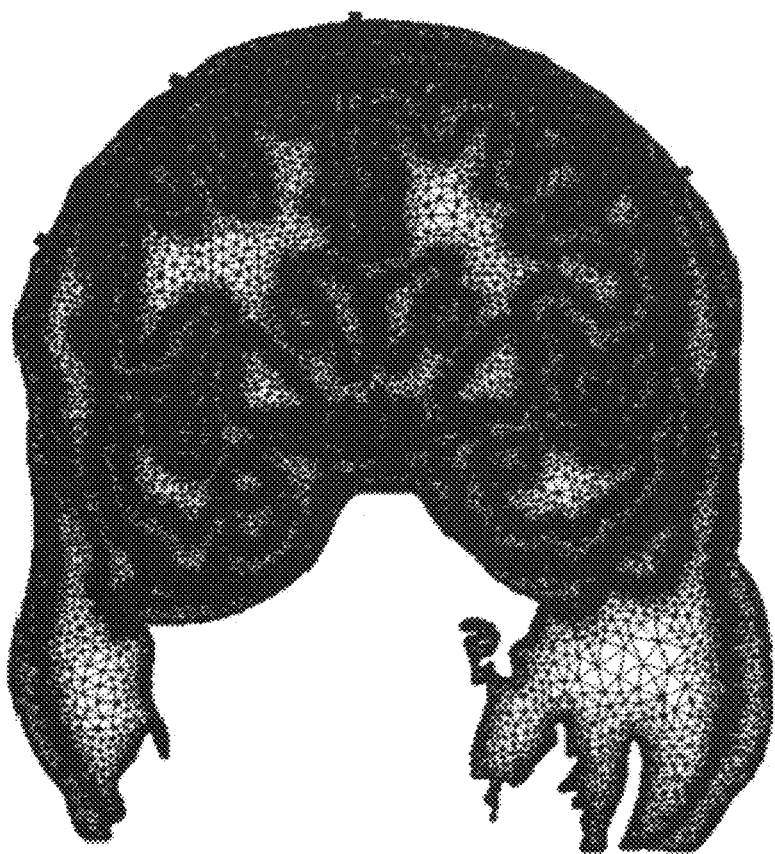
FIG. 3 illustrates a human brain having a mesh for finite element modeling applied thereto.

In pilot work, a 2-D model has been developed of a single MRI slice through a head, in accordance with an alternative embodiment. FIG. 3 illustrates a human brain having a mesh for finite element modeling applied thereto (see also FIG. 7B which illustrates a finite element mesh with mesh elements of different sizes and shapes). The mesh includes elements of different shapes and sizes that have different resistivities assigned to them. In the 2-D embodiment, current paths after transcranial stimulation can be predicted, e.g., in an anatomically correct coronal section through the upper limb representation of motor cortex, using FEM methods.

Current densities are obtained in this embodiment for a coronal MRI section (6.5 mm) through the upper limb motor cortex. The modeling procedes in two steps: segmentation to identify tissue compartment boundaries and resistivities, and then implementation of a finite element model to solve the forward problem (modeling measurements using given parameter values) for current densities.

Segmentation

Figure 4:
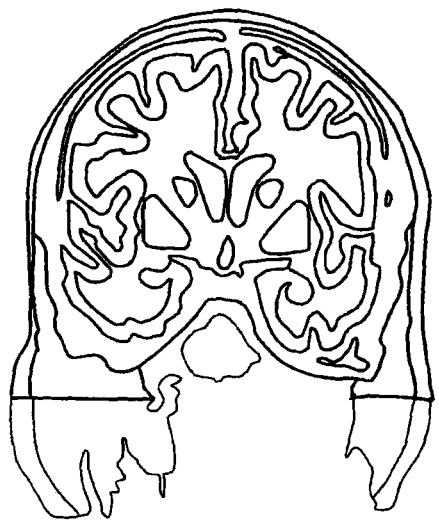
FIG. 4 illustrates a human brain having several tissue compartments identified and segmented in accordance with an exemplary embodiment.

The scanned image may be contrast enhanced and then preliminary tissue compartment boundaries are identified automatically, semi-automatically or manually, and in some cases, using commercially available software (e.g., Canvas). FIG. 4 illustrates a human brain having several tissue compartments identified and segmented according to their different resistivities in accordance with some embodiments. The tissue compartments that are segmented in the representation of FIG. 4 include cerebrospinal fluid (CSF) at 65 ohm-cm, white matter at 85 ohm-cm, blood at 160 ohm-cm, skin at 230 ohm-cm, gray matter at 300 ohm-cm, soft tissue at 500 ohm-cm, cancellous bone at 2500 ohm-cm, and compact bone at 16000 ohm-cm.

Most of the tissue resistivity estimates were taken from Haueisen et al. (1997), which summarized resistivity values from many studies and provided mean values for tissue compartments. The exception is the resistivity for white matter, which was taken from the summary of Geddes and Baker (1967). We used a longitudinal (as compared to transverse) estimate obtained from the internal capsule of the cat (Nicholson, 1965). A longitudinal estimate is appropriate because this is the dominant orientation of fibers for a small electrode positioned tangential to a site on cerebral cortex. As mentioned before the values for bone were taken from Goncalves et al., 2003; Oostendorp et al., 2000.

Figure 5:
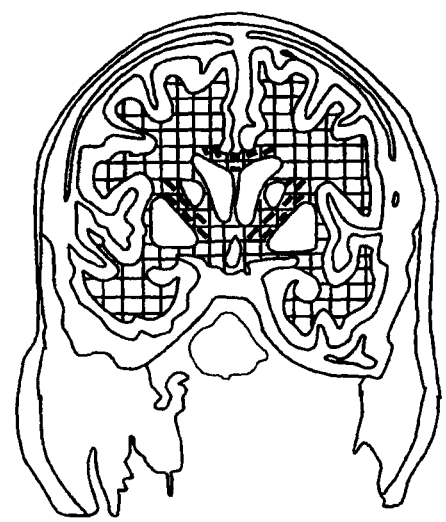
FIG. 5 illustrates a human brain having several tissue compartments having different anisotropic resistivities identified and segmented, and having a mesh for anisotropic finite element modeling applied thereto.

The preliminary boundaries are then superimposed over an original MRI image, such as the MRI image illustrated in FIG. 5. Final segmentation of tissue compartments may be completed by hand. Matching MRI and anatomical sections from human brain atlases of Talairach and Tournoux, and Schaltenbran and Wahren (Nowinski et al., 1997, citation below and hereby incorporated by reference) greatly aided in identifying gray matter compartments, particularly deep brain nuclei.

In FIG. 5, a grid is shown which serves as a finite element mesh, and the elements have directionalities or anisotropies ascribed thereto and illustrated with the slanted lines inside the elements of the grid. These directionalities correspond to directionalities of the nerve fibers.

Finite Element Modeling

2-D current densities may be expressed as amps per meter, while 3-D current densities may be expressed in amps per square centimeter that would be applied in a 3-D model. Units of coulombs per square centimeter may also be used for modeling pulses.

Bilateral electrode placements (and an applied potential difference of 100 V) are calculated for the segmented section, using a FE model generated using FEMLAB (Comsol Pty Ltd, Burlington Mass.). A mesh may be constructed by first detecting edge contours of each segment within the image, then converting the region within each contour into 2 D subdomains. Meshing of the entire structure may be carried out using standard FEMLAB meshing routines, requiring that minimum element quality be 0.1, (quality parameter varies between 0 and 1, acceptable minimum mesh quality is 0.6). For example, the modal value of mesh quality may be approximately 0.98. Triangle quality is given by the formula: $q=4\sqrt{3}a \div [h_1^2+h_2^2+h_3^2]$, where a is the triangle area and $h_1$, $h_2$, and $h_3$ are side lengths of the triangle; and q is a number between 0 and 1. If q>0.6, the triangle is of acceptable quality, and q=1 when $h_1=h_2=h_3$. If triangle elements have low q they are typically long and thin, which may result in the solution on the mesh being inaccurate.

The linear meshes for the model illustrated at FIG. 3 contained approximately 180,000 elements and 364,000 degrees of freedom. Solution of the models to a relative precision of less than $1 \times 10^{-6}$ involved around 27 seconds on a Dell Workstation (2.4 GHz processor, 2 GB RAM) running Linux (RedHat 3.0 WS).

Modeling Results

Figure 6A:
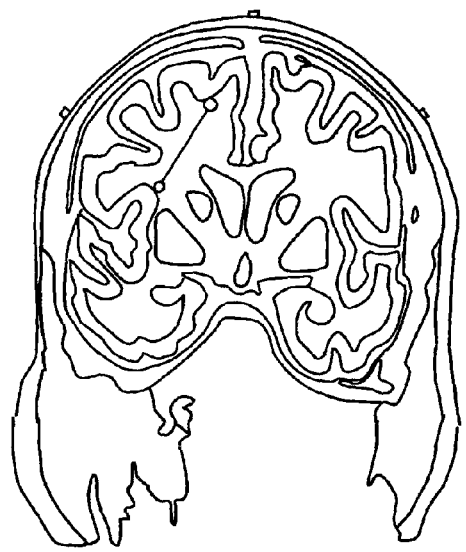
FIG. 6a illustrates a human brain with two selected electrode locations and a current path defined therein.

The modeling results are illustrated at FIGS. 6A-6D. FIG. 6A includes a representation of a human brain with multiple compartments segmented by values of resistivity and having line boundaries obtained from an isotropic model. FIG. 6A also illustrates a pair of electrode locations "+" and "−". A current path of interest (CPI) is also indicated in FIG. 6A.

Figure 6B:
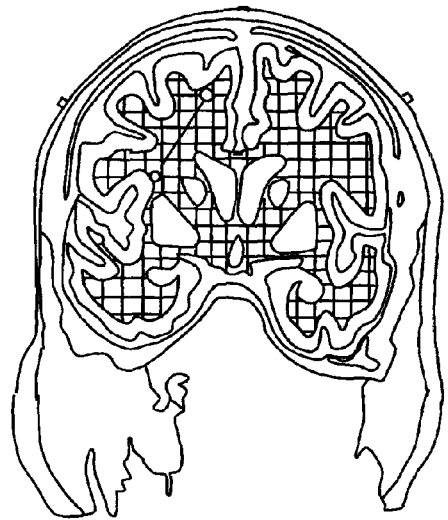
FIG. 6b illustrates the human brain of FIG. 6a having a mesh for finite element modeling applied thereto.
Figure 6C:
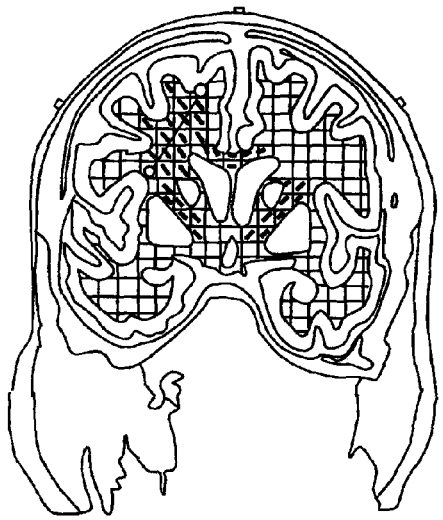
FIG. 6c illustrates the human brain of FIG. 6b with anisotropies ascribed to elements of the mesh.

The image of FIG. 6B has a matrix or grid of squares, rectangles, or other polygons such as triangles over the features illustrated in FIG. 6A. FIG. 6C illustrates the anisotropies as directional lines within at least some of the polygons that make up the grid.

Figure 6D:
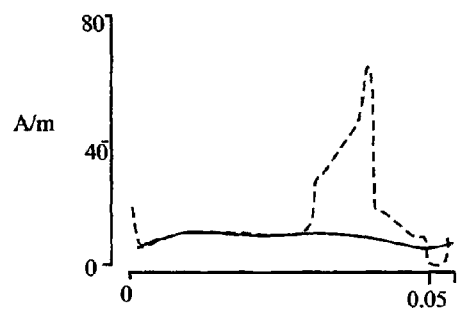
FIG. 6d shows plots of current density through identical regions of isotropic and anisotropic models.

The line plots in FIG. 6D are of current densities through identical locations along the current path of interest CPI illustrated at FIGS. 6A, 6B and 6C. The solid line in FIG. 6D is the current density obtained from the isotropic model represented at FIG. 6A, while the dashed line in FIG. 6D is the current density obtained from the anisotropic model of FIG. 6C. In the illustrated example, a peak P around 68 A/m was observed for the anisotropic model, while the isotropic model provided a maximum of 16 A/m for the homogeneous white matter region studied along the CPI. As can be seen from this result, tissue anisotropies have a significant influence on the location of the hot spots.

Figure 7A:
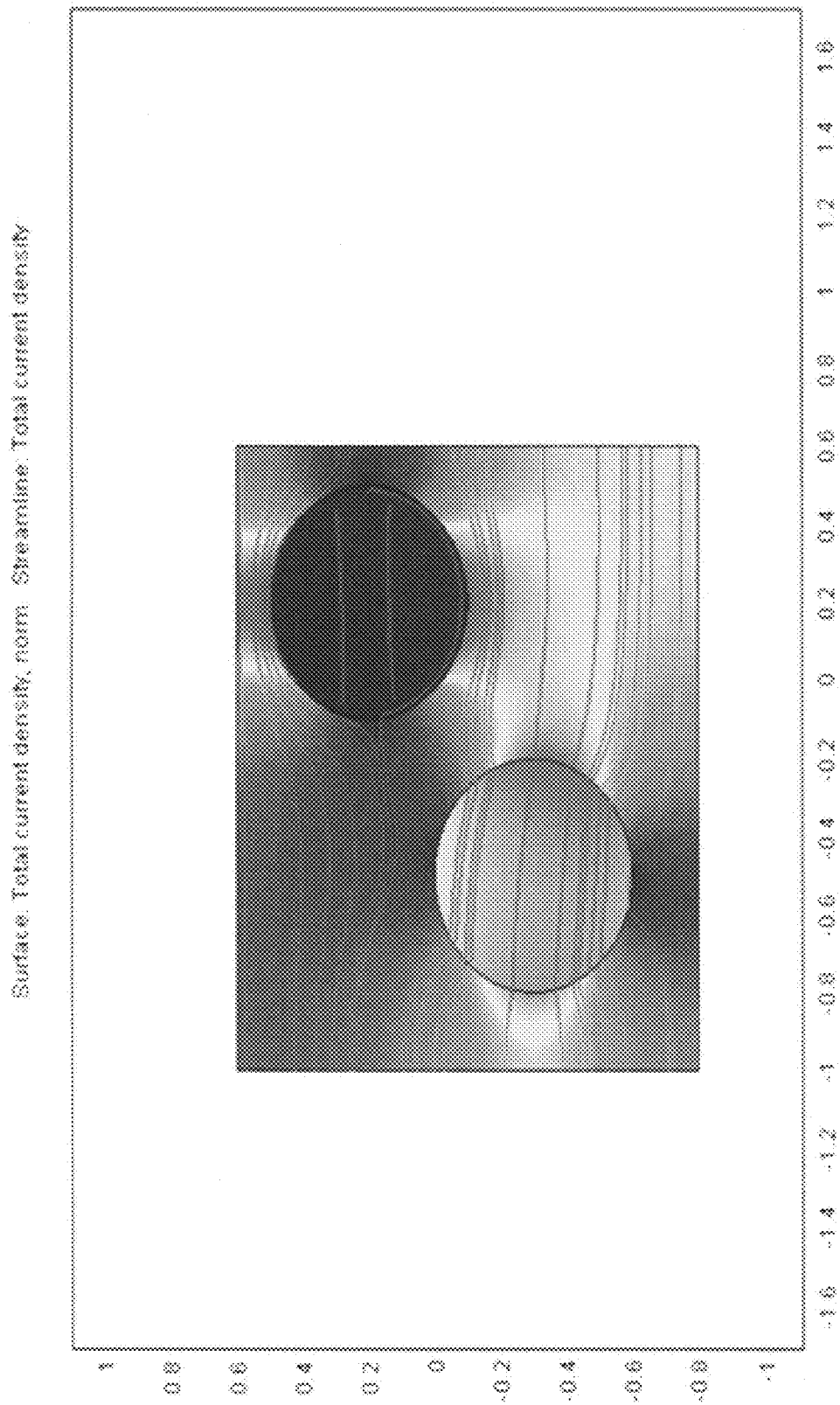
FIG. 7a illustrates current density variations around areas of varying anisotropic resistivities.
Figure 7B:
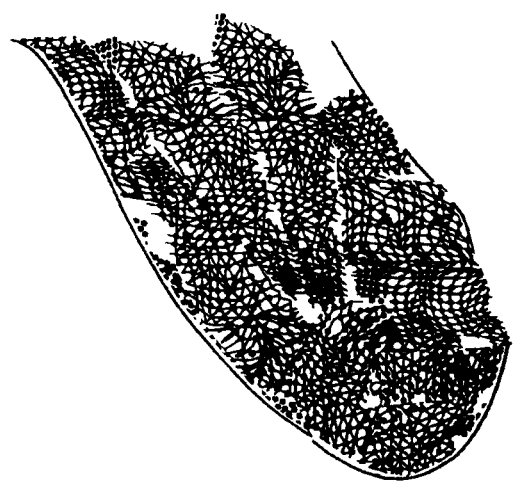
FIG. 7b illustrates a finite element mesh with mesh elements of different sizes and shapes.

The GETs model demonstrates some expected and unexpected results. As expected, there is a concentration of current below the electrodes. However, the optimal current path demonstrated is not always the path of least resistance. There are regions of high current density where there is a high conductivity inclusion within a sphere of lower conductivity (see zones at the pituitary stalk and the ventricle) (see Knudsen 1999 and Grimnes, S. and Martinsen O. G. 2000, citations below and hereby incorporated by reference, for detailed explanations of why this occurs). FIG. 7A illustrates this effect. The effect appears to create hot spots of electric field induced in the surrounding low conductivity region. The current increase is greatest in the vicinity of interfaces that lie perpendicular to the current flow. Some of these current densities are substantially above the surrounding area and significantly distant to the placement of the electrodes. In this context, the challenge is to determine electrode locations such that unwanted activation is minimized, while stimulating targeted areas efficiently.

Tissue anisotropy is advantageously modeled in accordance with some embodiments, and it has been modeled for an injection current in the brain. Models of further embodiments include anisotropic modeling of blood vessels and directionality of muscle fibers. Because the GETs model is based on MRI images and/or CAT scans of individuals, it also adjusts to developmental and individual differences in brain structure. Among the most significant of these are the differences in bone structure.

Figure 8:
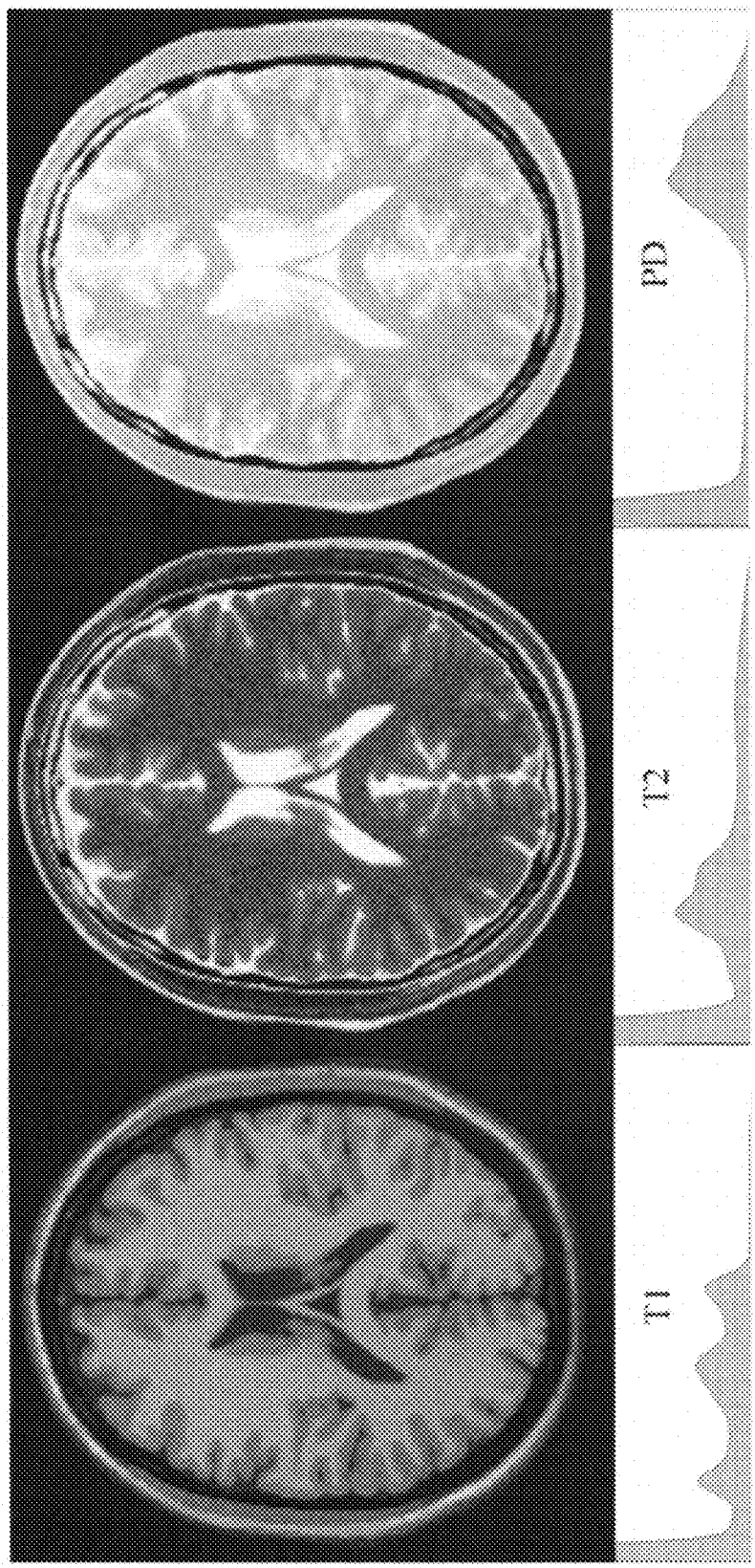
FIG. 8 illustrates MRI images of three different types: T1, T2 and PD.

FIG. 8 illustrates MRI images of three different types: T1, T2 and PD. Below each MRI image is a histogram of pixel intensities shown in the corresponding MRI image. As is well known to persons having ordinary skill in the art, each MRI image includes multiple pixels (or voxels), and each pixel (or voxel) has a value (often called intensity). For images taken with an 8-bit resolution MRI instrument, each pixel value (or pixel intensity) may range from 0 to 255. The histogram for the T1 MRI image shows three peaks which may correspond to three distinct tissue types having three different resistivities. The histogram for the T2 MRI image shows one, or possibly two, peaks, and the histogram for the PD MRI image shown one peak at a different resistivity than T2 or T1. By utilizing information from multiple images of different MRI types, it is possible to enhance segmentation based on pixel intensities.

In some embodiments, utilizing information from multiple images (e.g., images of different MRI types) includes generating a combined image from the multiple images. One way to generate a combined image is by interleaving the multiple images.

Figure 11:
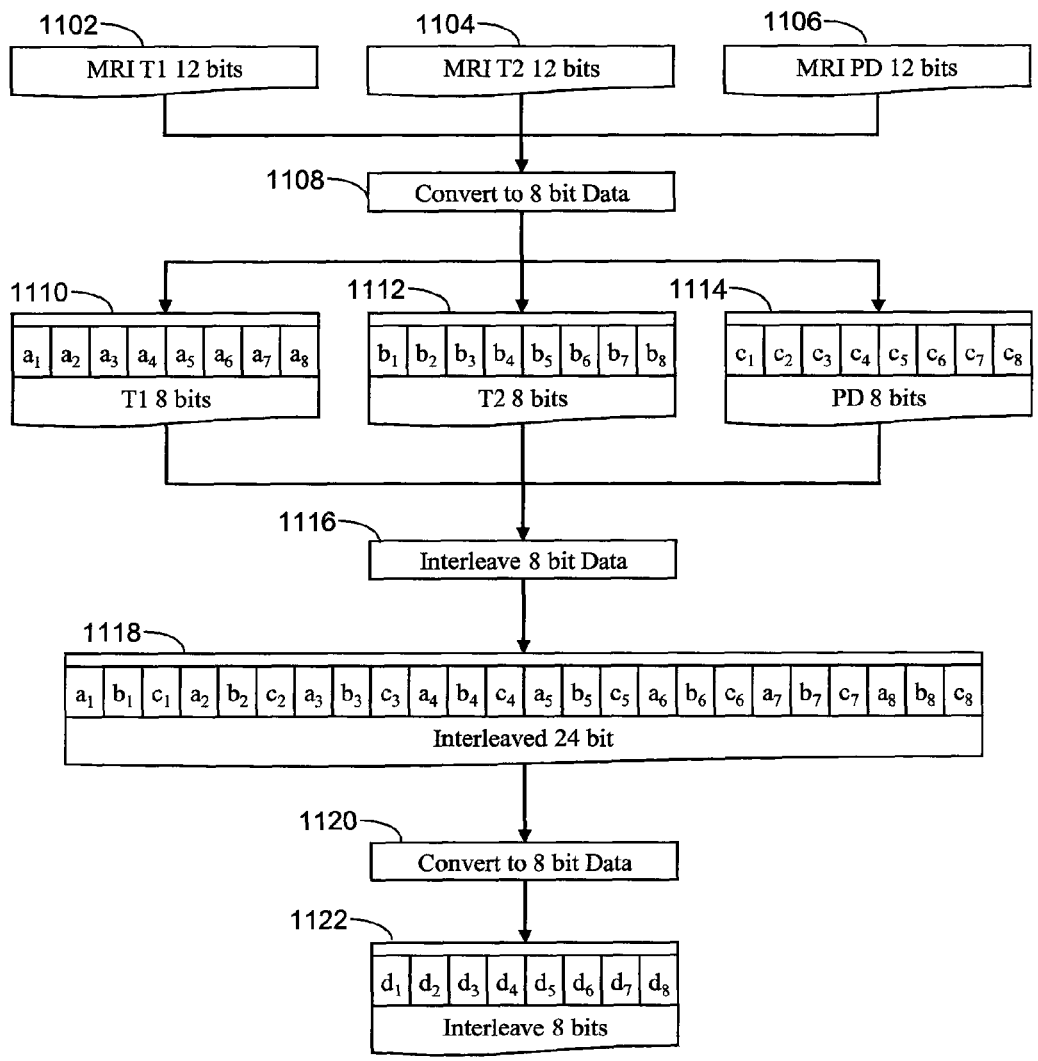
FIG. 11 illustrates a method of generating a combined image in accordance with some embodiments.

FIG. 11 illustrates a method of generating a combined image by interleaving multiple images in accordance with some embodiments. The method starts with multiple images (e.g., 1102, 1104, and 1106) as input. The multiple images may comprise any combination of two or more of: T1, T2, and proton density MRI images; a magnetic resonance angiography image; and an X-ray computed-tomography image. Typically, three or more of T1, T2, and proton density MRI images; a magnetic resonance angiography image; and an X-ray computed-tomography image are used. For example, the multiple images include a T1 MRI image 1102, a T2 MRI image 1104, and a PD MRI image 1106.

Typically, the multiple images are registered (i.e., a same portion of each of the multiple images corresponds to a same portion of the biological structure). In some cases, raw images of a subject taken with a same MRI instrument in different image modes are registered. However, when the raw images are not registered (e.g., due to patient movement or multiple images taken with different instruments), one or more images of the raw images may be translated, rotated, and scaled to obtain the registered multiple images. The methods for registering the raw images are well known in the art, and thus are not repeated herein for brevity.

In addition, the multiple images are typically normalized. In some embodiments, the normalization is performed by adjusting the intensity of each image so that the highest pixel value in each image corresponds to a predefined value. In some other embodiments, the normalization is performed by adjusting the intensity of each image so that a pixel corresponding to a certain biological medium (e.g., cerebrospinal fluid) has an intensity matching a predefined value.

In some embodiments, each MRI image is converted (1108) to an image of a predefined intensity resolution. For example, when each pixel of the multiple images (1102, 1104, and 1106) includes 12-bit data, such pixel can be converted into 8-bit data pixel. In some embodiments, the conversation is performed by selecting a predefined number of most significant bits (e.g., eight left-most bits for a conversion from 12-bit data to 8-bit data). In some other embodiments, the conversion is performed based on normalization. For example, the 12-bit data is converted into the 8-bit data by dividing the 12-bit data with the maximum possible value of 12-bit data (e.g., 4095) and multiplying with the maximum possible value of 8-bit data (e.g., 255). As a result, converted images (e.g., 1110, 1112, and 1141) are obtained. The converted image 1110, which includes 8-bit data and corresponds to the T1 MRI image 1102, includes eight bits $a_1$ through $a_8$ for each pixel. The converted image 1112, which includes 8-bit data and corresponds to the T2 MRI image 1104, includes eight bits $b_1$ through $b_8$ for each pixel. The converted image 1114, which includes 8-bit data and corresponds to the PD MRI image 1106, includes eight bits $c_1$ through $c_8$ for each pixel.

The converted images (e.g., 8-bit data), or the original images (e.g., 12-bit data) are interleaved (1116) to generate an interleaved image 1118. When interleaving three 8-bit converted images (e.g., 1110, 1112, and 1114), the interleaved image 1118 includes 24-bit data (e.g., [$a_1$, $b_1$, $c_1$, $a_2$, $b_2$, $c_2$, $a_3$, $b_3$, $c_3$, $a_4$, $b_4$, $c_4$, $a_5$, $b_5$, $c_5$, $a_6$, $b_6$, $c_6$, $a_7$, $b_7$, $c_7$, $a_8$, $b_8$, and $c_8$]).

In some embodiments, the interleaved image 1118 is converted into an image 1122. In some embodiments, the conversion is performed by selecting a predefined number of most significant bits (e.g., eight left-most bits for a conversion from 24-bit data to 8-bit data, such as [$a_1$, $b_1$, $c_1$, $a_2$, $b_2$, $c_2$, $a_3$, $b_3$]). In some other embodiments, the conversion is performed based on normalization. For example, the 24-bit data is converted into the 8-bit data by dividing the 24-bit data with the maximum possible value of 24-bit data (e.g., 16,777,215) and multiplying with the maximum possible value of 8-bit data (e.g., 255).

The output of the interleaving process may vary depending on the order of the multiple images. For example, a different order of the T1, T2, and PD MRI images may be used (e.g., T1, PD, and T2; T2, T1, and PD; T2, PD, and T1; PD, T1, and T2; PD, T2, and T1).

Alternatively, a weighted-sum image may be used. Each pixel (or voxel) in the weighted-sum image has an intensity based on a weighted-sum of intensities of corresponding pixels (or voxels) in the multiple images. In some embodiments, this relationship can be expressed as:

$$I_c = \Sigma w_j \cdot I_j, \quad \text{(Eq. 1)}$$

where $I_c$ is an intensity of a respective pixel in the combined image, $w_j$ is a weight for a j-th image of the multiple images, and $I_j$ is an intensity of a corresponding pixel in the j-th image of the multiple images. In some embodiments, the intensity of the respective pixel in the combined image also includes higher-order terms (e.g., a second power and/or a third power of the intensity of the corresponding pixel).

In some embodiments, the weights (e.g., $w_j$) are determined using least-squares methods on a training set of images. The training set of images includes multiple images that include regions of known electrical properties.

In such embodiments, the intensity of each pixel in the combined image may directly correspond to an electrical property of a region of a biological structure corresponding to the pixel. For example, the intensity of each pixel in the weighted-sum image may represent an electrical property (e.g., resistivity) of the corresponding region (e.g., white matter) of the biological structure.

Figure 9:
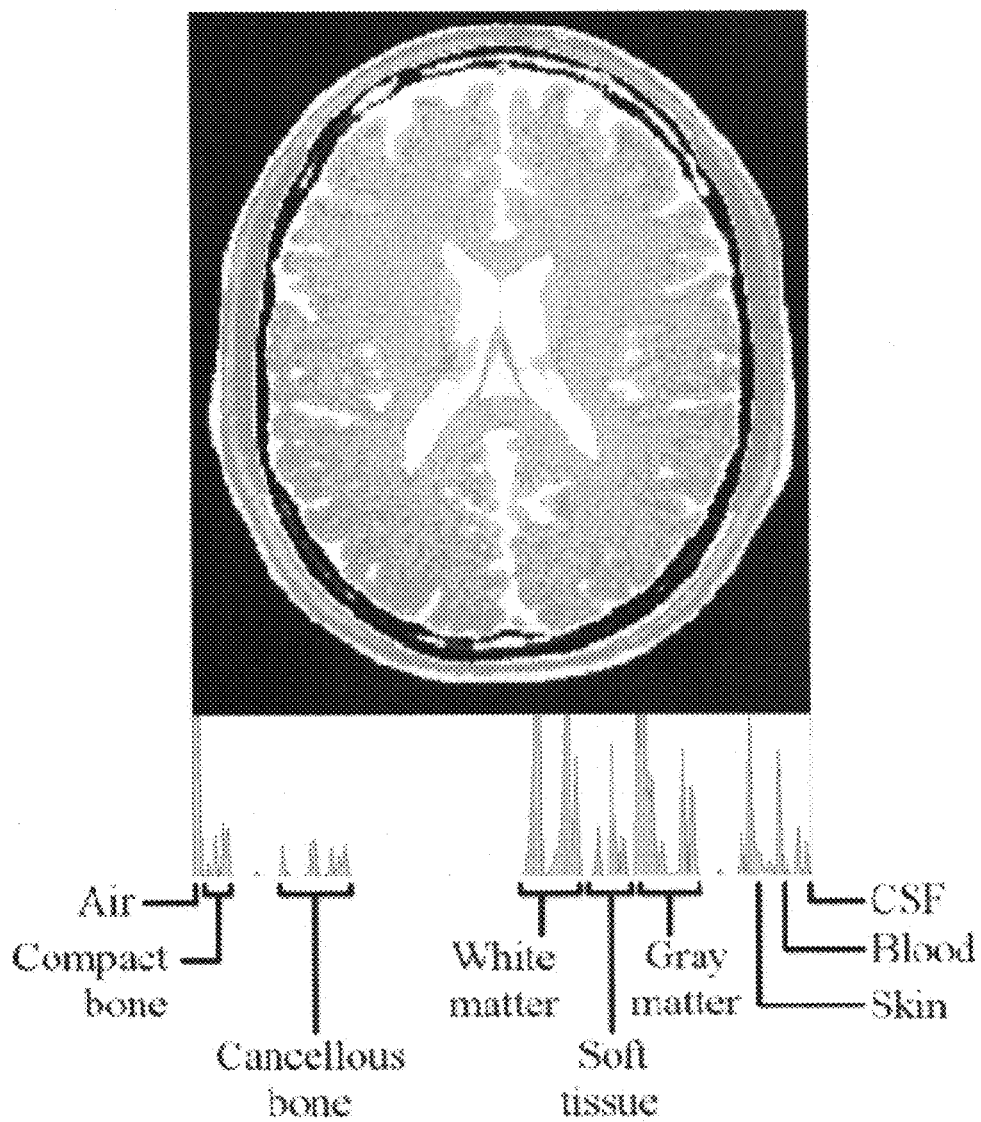
FIG. 9 illustrates an MRI image and a histogram of pixel intensities (or voxel intensities).

The combined image shown in FIG. 9 is an interleaved image of T1, T2, and PD MRI images of a brain. FIG. 9 is a prophetic example of a combined image and a histogram of pixel intensities (or voxel intensities) showing multiple peaks. The histogram may be generated based on pixels in the illustrated slice of an image. Alternatively, the histogram may be generated based on selected voxels (e.g., all the voxels corresponding to a selected organ or region of a subject). The histogram for the combined image shown in FIG. 9 resolves multiple peaks corresponding to various tissue types including compact bone, cancellous bone, white matter, soft tissue, gray matter, skin, blood and cerebrospinal fluid. Other resolvable tissues may include cancerous tissue, inflammatory tissue and ischemic tissue, as well as eye fluid. By having enhanced resolution of tissues, it is possible to assign more correctly the resistivities or other electrical values of brain or other body tissues, and thereby calculate more precisely the current or other electrical input to be applied for monitoring or therapeutic purposes (e.g., for killing cells, such as tumor cells).

Identifying Tissue Resistivities Based on MRI Data

A relationship of tissue resistivity to the MRI pixel intensity can be expressed by the formula:

$$R(v) = K(1-v)^E + D, \quad \text{(Eq. 2)}$$

where R=Resistivity; v=Normalized value of MRI data; K=Multiplier value; E=Exponent; and D=Density value.

The v value can be an intensity value of either a simple MRI image or a combined image of multiple MRI images or multiple types of MRI images, normalized by the maximum possible value of the MRI data values or combined values. For example, when each pixel or voxel of the MRI data is represented by an 8 bit data, the v value for each pixel or voxel is ([the intensity value from the combined image]/[the maximum possible value from an 8 bit data (i.e., 255)]). Therefore, v has a value between zero and one.

For the interleaved image of T1, T2, and PD MRI images, exemplary constants for the equation 2 include K=16000, E=4 and D=65. Thus, for the interleave image, a region corresponding to a v value of 1 (e.g., cerebrospinal fluid) has an R value of 65 (Ohm-cm).

In some embodiments, the equation described above is used to calculate the tissue resistivity when v has a value larger than 0.02. When v has a value that is equal to or smaller than 0.02, a predefined resistivity (e.g., 5 M ohm-cm) is used.

It is understood that persons having ordinary skill in the art recognize the reciprocal relationship between the resistivity and the conductivity. Therefore, the equation described above (or a reciprocal or multiplicative inverse function thereof) may be used in determining the tissue conductivity.

In addition, anisotropies/directionalities can be inferred from the anatomy or determined based on the MRI data, or a combination thereof. A direct determination is accomplished by diffusion tensor MRI (DT-MRI, or DTI). The indirect determination is accomplished by inferring the direction of fibers, specifically nerve fibers, by the general anatomy. DT-MRI data are sometimes called anisotrophic MRIs. In some embodiments, the anisotropies are added to the combined image to obtain anisotropic tissue properties (e.g., anisotropic electrical properties).

Computer Systems and Methods

Figure 12:
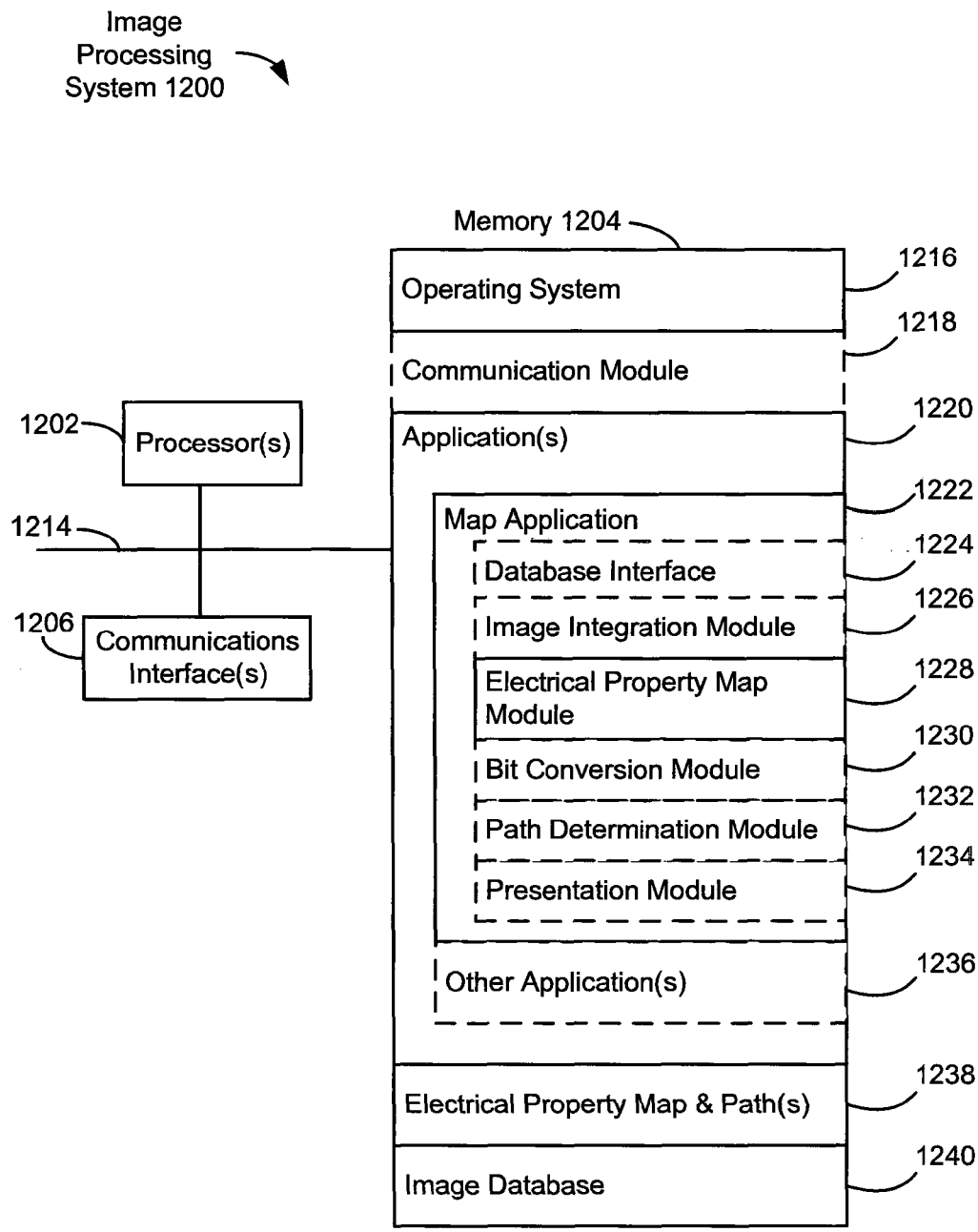
FIG. 12 is a block diagram illustrating a system for processing multiple images in accordance with some embodiments.

FIG. 12 is a block diagram illustrating an image processing system 1200 for processing multiple images in accordance with some embodiments. The image processing system 1200 typically includes one or more processors (CPUs) 1202, memory 1204, one or more network or other communications interfaces 1206, and one or more communication buses 1214 for interconnecting these components. In some embodiments, the communication buses 1214 include circuitry (sometimes called a chipset) that interconnects and controls communications between system components. In some other embodiments, the image processing system 1200 includes a user interface (not shown) (e.g., a user interface having a display device, a keyboard, and a mouse or other pointing device).

Memory 1204 includes high-speed random access memory, such as DRAM, SRAM, DDR RAM or other random access solid state memory devices; and may include non-volatile memory, such as one or more magnetic disk storage devices, optical disk storage devices, flash memory devices, or other non-volatile solid state storage devices. Memory 1204 may optionally include one or more storage devices remotely located from the CPU(s) 1202. Memory 1204, or alternately the non-volatile memory device(s) within memory 1204, comprises a non-transitory computer readable storage medium. In some embodiments, memory 1204 or the computer readable storage medium of memory 1204 stores the following programs, modules and data structures, or a subset thereof:

Operating System 1216 that includes procedures for handling various basic system services and for performing hardware dependent tasks;

Network Communication Module (or instructions) 1218 that is used for connecting the image processing system 1200 to other computers via the one or more communications interfaces 1206 and one or more communications networks, such as the Internet, other wide area networks, local area networks, metropolitan area networks, and so on;

Application(s) 1220 that include one or more programs for execution by the one or more processors 1202;

Electrical Property Map & Path(s) 1238 that include one or more electrical property maps of one or more biological structures and one or more paths within the one or more electrical property mpas (e.g., current path); and Image Database 1240 that includes multiple images for processing by the one or more processors 1202 and one or more combined images.

The Application(s) 1220 includes a map application 1222 include the following interfaces, modules, or a subset thereof:

Database Interface 1224 that assists retrieving, storing, or updating data in the Image Database 1238;

Image Integration Module 1226 that generates combined images from multiple images;

Electrical Property Map Module 1228 that generates an electrical property map;

Bit Conversion Module 1230 that converts M-bit data to N-bit data, where N is distinct from M (e.g., conversion from 12-bit data to 8-bit data);

Path Determination Module 1232 that identifies a current path in accordance with the electrical property map; and Presentation module 220 that formats results from the Electrical Property Map Module 1228 and/or the Path Determination Module 1232 for display.

Each of the above identified modules and applications correspond to a set of instructions for performing one or more functions described above. These modules (i.e., sets of instructions) need not be implemented as separate software programs, procedures or modules, and thus various subsets of these modules may be combined or otherwise re-arranged in various embodiments. In some embodiments, memory 1204 may store a subset of the modules and applications identified above. Furthermore, memory 1204 may store additional modules, applications, and data structures not described above.

FIGS. 13A and 13B are flow diagrams illustrating a method 1300 for generating an electrical property map in accordance with some embodiments. The method 1300 is performed at a computer system (e.g., the image processing system 1200) having one or more processors and memory storing one or more programs for execution by the one or more processors.

The computer system accesses (1302) multiple images of a biological structure (e.g., T1, T2, and PD MRI images shown in FIG. 8). For example, the multiple images may be stored in the image database 1240 (FIG. 12). Alternatively, the computer system may access the multiple images stored in a remote computer system (e.g., an MRI instrument located remotely or a computer system coupled with the remotely-located MRI instrument).

In some embodiments, the multiple images of the biological structure include (1304) two or more of: T1, T2, and proton density MRI images; a magnetic resonance angiography image; and an X-ray computed-tomography image.

In some embodiments, the multiple images of the biological structure include (1306): T1, T2, and proton density MRI images (e.g., see FIG. 8).

The computer system generates (1308) an electrical property map of at least a portion of the biological structure in accordance with two or more of the multiple images. For example, the combined image shown in FIG. 9 serves as an electrical property map of a slice of a brain. Such electrical property map may represent a conductivity or resistivity of tissue at each portion of the biological structure shown in the electrical property map. In some cases, the electrical property map may represent a polarity of various cells in each portion of the biological structure shown in the electrical property map.

In some embodiments, generating the electrical property map includes (1310): generating a combined image of T1, T2, and proton density MRI images of the biological structure (e.g., FIG. 9); and determining respective electrical property values for respective regions of the combined image (e.g., determining resistivity for each pixel or voxel of the combined image). In some embodiments, the computer system converts pixel intensities to obtain electrical property values.

In some embodiments, generating the electrical property map includes (1312): generating a combined image of at least the portion of the biological structure; and determining respective electrical property values for respective regions of the combined image. For example, the computer system converts pixel intensities to electrical property values (e.g., using the Equation 2).

In some embodiments, each image of the biological structure includes (1314) a plurality of respective regions (e.g., pixels or voxels), and each region has an intensity value represented with multiple data bits (e.g., 8-bits). Generating the combined image includes, for each region corresponding to at least the portion of the biological structure, interleaving at least a subset of the multiple bits from respective images (e.g., see FIG. 11).

In some embodiments, the respective electrical property values include (1316) respective tissue resistivity values. The computer system determines respective tissue resistivity values in accordance with an equation:

$$R(v) = K(1-v)^E + D,$$

where R is a respective tissue resistivity value, K is a multiplier value, v is a respective normalized numeric value stored in the combined image, E is an exponent, and D is a density value.

In some embodiments, the computer system determines (1318) respective conductivity values for respective regions of the combined image. For example, the computer system may determine respective resistivity values and then calculate reciprocal values of the respective resistivity values.

In some embodiments, generating the electrical property map includes (1320) generating a weighted-sum image of the two or more of the multiple images. For example, the computer system may determine the intensity of each pixel in a combined image by using the equation 1 described above. In some embodiments, the weights used in generating the weighted-sum image are determined in accordance with an approximation method (e.g., least-squares).

In some embodiments, the electrical property map includes a plurality of respective regions (e.g., pixels or voxels), and each region has an electrical property value that is isotropic (e.g., a conductivity or resistivity that is orientation-independent).

In some embodiments, generating the electrical property map includes obtaining a plurality of anisotropic electrical property values, and adjusting the electrical property map in accordance with the plurality of anisotropic electrical property values (e.g., adding respective anisotropic electrical property values to corresponding isotropic electrical property values in the electrical property map). Obtaining the plurality of anisotropic electrical property values typically includes processing one or more diffusion-weighted images of the biological structure. For example, the one or more diffusion-weighted images of the biological structure may be analyzed (e.g., using the diffusion tensor analysis method or the Q-ball analysis method) to obtain the plurality of anisotropic electrical property values.

The computer system provides (1322, FIG. 13B) at least a subset of the electrical property map. For example, the computer system displays at least the subset of the electrical property map. Additionally or alternatively, the computer system transmits at least the subset of the electrical property map to a second computer system typically located remotely from the computer system. The second computer system may be located at a hospital or in a doctor's office so that a physician or a surgeon may review the electrical property map.

In some embodiments, the multiple images include (1324) a functional MRI image. The computer system overlays (1324) at least a subset of the functional MRI image onto the electrical property map of at least the portion of the biological structure.

In some embodiments, the computer system identifies (1326) one or more electrode sites for providing stimulation of at least a respective region of the biological tissue in accordance with at least the subset of the electrical property map. The details of selection of one or more electrode sites are described in detail with respect to the section entitled "Stimulation Site Selection."

In some embodiments, the computer system identifies (1328) one or more inductance sites for providing magnetic pulse stimulation of at least a respective region of the biological tissue in accordance with at least the subset of the electrical property map.

Individual Differences and Developmental Variations

Bone is the highest resistivity tissue in the body thus making the skull a significant barrier to injection currents. There are also considerable variations in skull thickness and density between sites within and between individuals. The cranial sutures, penetrating vessels and individual anomalies provide low resistivity paths through the skull that are important sources of individual variation.

Developmentally, the presence of highly vascularized fontanel in young children provides a path for current through the skull, because of the fontanel's much lower resistivity (scalp: 230 ohm-cm; blood: 160 ohm-cm; bone 7560 ohm-cm) compared with the surrounding bone. These fontanels are substantially closed by 1.5 years to form the sutures present in the adult skull (Law, 1993, citation below and incorporated by reference). The sutures remain open for some time in many adults, and do not close at all in some aged individuals, although in others they close completely. By adjusting for these differences rather than simply increasing the current, we are able to significantly reduce currents needed to stimulate the brain of an individual.

Figure 1A:
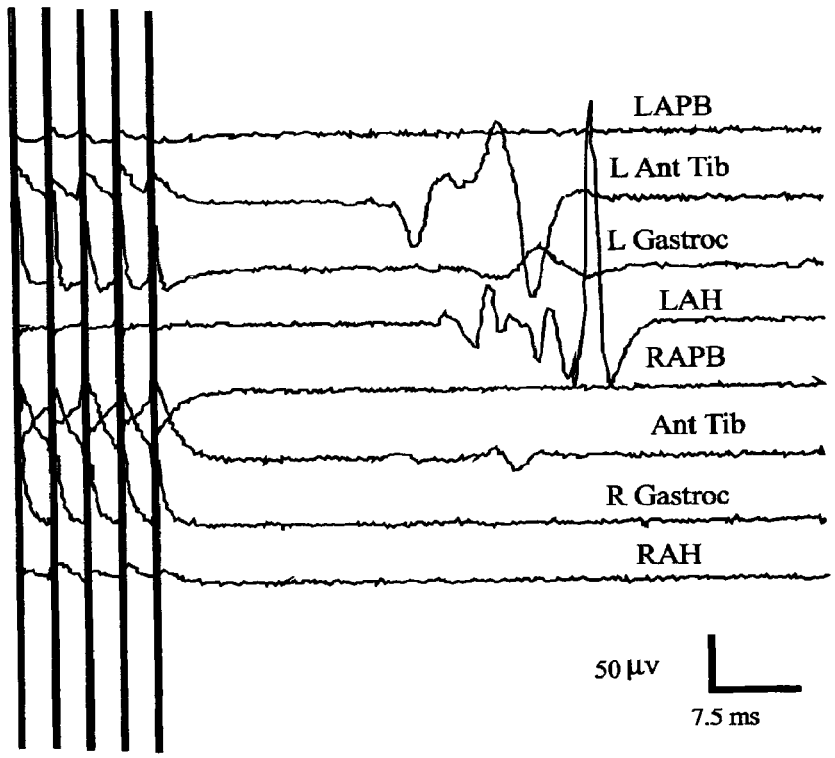
FIG. 1A illustrates tcMEP from a scoliosis patient.
Figure 1B:
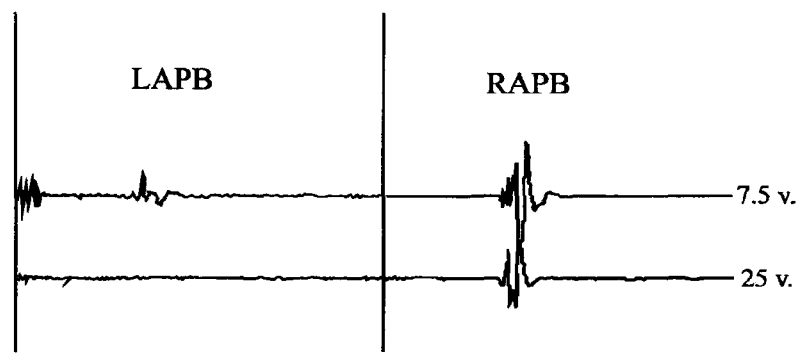
FIG. 1B illustrates tcMEP from an 86 year old male with a neck fracture.
Figure 2:
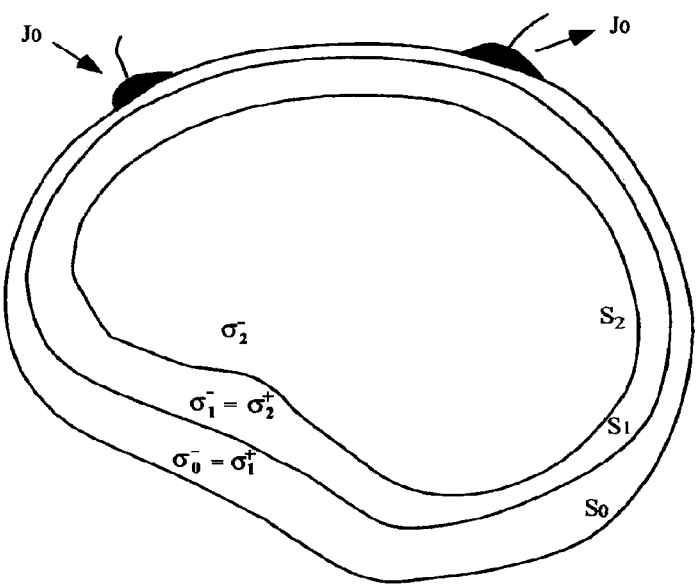
FIG. 2 illustrates a human head with materials of different conductivities conventionally identified and having two electrodes coupled therewith.

FIGS. 1A and 1B were introduced earlier. FIG. 1A shows MEPs evoked by transcranial stimulation in a 14 year old scoliosis patient. The electrode positions were approximately at C1 and C2 (10-20 system), with anodal stimulation applied at C2 (50V). The largest amplitude MEPs were evoked from muscles of the left foot (abductor hallucis) and leg (anterior tibialis), although smaller responses from the abductor hallucis muscle on the right side was also noted. No responses were recorded in the abductor pollicic brevis muscles of either hand. These relatively low current responses were obtained by slight adjustments in electrode locations. Similar adjustments varying from patient to patient may be used to optimize MEP signals.

In alternative embodiments, it is possible to reduce the level of stimulation for intraoperative monitoring and improve our understanding of what is occurring with tcMEP. In some embodiments, however, significant further improvement is achieved. Additional improvements are provided in the model by: 1) utilizing a three-dimensional GETs model; 2) improving the detail in the images to account for blood vessels, finer nerve tracks and bone anomalies; 3) adding into the model the effects of capacitance found at tissue boundaries; 4) verifying the model with direct brain measurements; or 5) by applying findings to the motor cortex in refractory Parkinsonism patients, or combinations thereof.

In one embodiment, GETs models are provided in 3-D, and finer detail is applied to the images, while effects of capacitance are added. As a result, the electrical property (or properties) represented by the electrical property map changes from resistivity to impedance.

Figure 10:
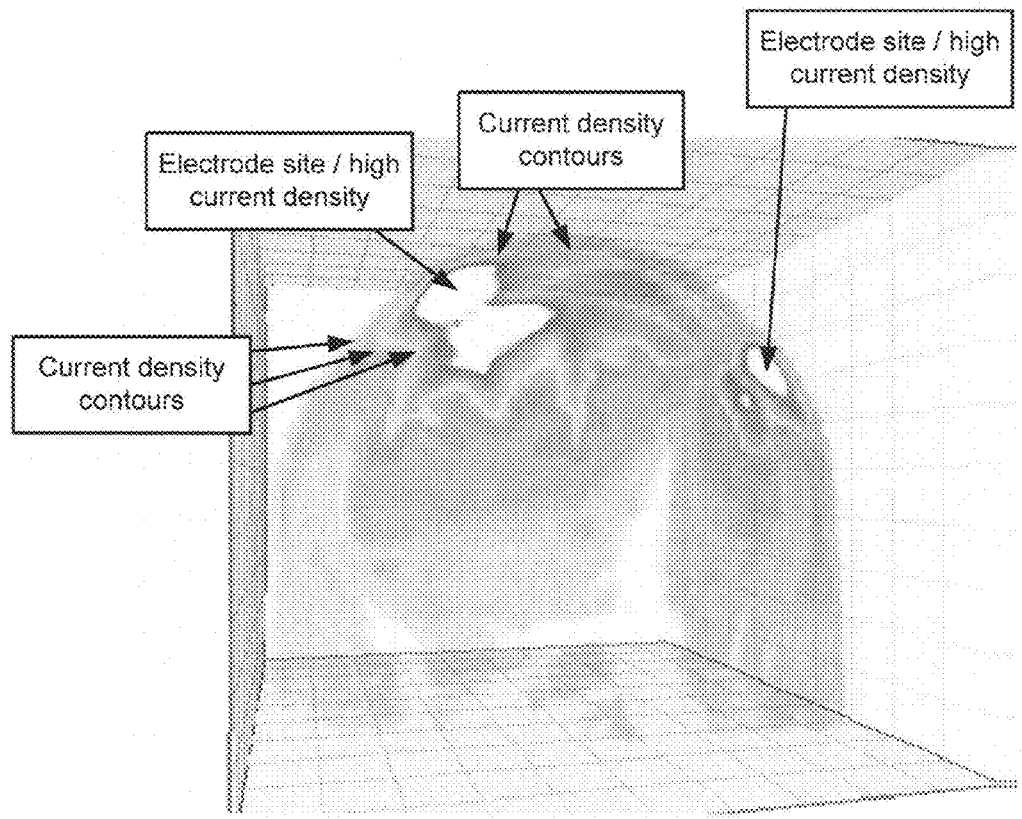
FIG. 10 illustrates three-dimensional modeling of current densities applied to a human brain coupled with two electrodes.

FIG. 10 illustrates three-dimensional modeling of current densities applied to a human brain coupled with two electrodes. FIG. 10 shows contours of constant current densities. FIG. 10 illustrates the high current density around the electrodes and changing current densities along any current path that traverses multiple tissues. In one embodiment, the images are segmented, a FE mesh is generated, and then the analysis is performed for isotropic models and/or anisotropic models with and without capacitance. In some embodiments, capacitance is an important factor as membrane capacitance at tissue boundaries as well as a significant factor in determining stimulus tissue penetration (see Grimnes S. Martinsen O. G 2000, citation below and incorporated by reference).

Segmentation

Segmentation, or the outlining, identifying, ascribing and/or assigning of resistivity values to MRI slices in 3-D, can be a difficult and arduous task. The effort involved may be significantly reduced by using commercial automated tissue analysis algorithms and services. For example Neuroalyse, Inc (Quebec, Canada), may be selected to perform such analysis. This system can perform more than 90% of the tissue segmentation and leave blank the areas of the tissue that the software is unable to resolve or where it is preferred to more particularly work with these areas. This automated segmentation is particularly advantageous as new MRI images have 2 mm thicknesses and record in three planes. The results are checked and any blank areas filled in by hand or other precision automation, or otherwise. Tissue resistivities are assigned, except tissue slices may be finer and values may be included for blood vessels and skull sutures. Resulting 2-D sliced images are then interleaved into a three 3-D model. A final 3-D segmentation and meshing may be performed using AMIRA (Mercury Computer Systems, Berlin, Germany) and the resulting 3-D models generated may be imported into Femlab (Comsol, Burlington Mass.) for FE calculation.

The 3-D images, with identified motor cortex, may be analyzed using the FE method. To identify the best sites for stimulation, an additional analysis may be performed by iteratively moving representative paired electrode locations across the scalp in the FE model and evaluating effects (e.g., the current density at the target site, such as motor cortex, and/or other sites). This targeting may be performed by having the computer systematically select and test for the highest current density at the target site for each of the locations of the traditional 10-20 system for electrode placements as current injection and extraction sites with a constant current pulse. In addition to the traditional 10-20 system, other sites that may be considered or selected may include eye lids, auditory canals and nasal passages as these additional locations represent avenues for bypassing the high resistivity of the skull bone. After the computer has grossly identified a pair of stimulation and extraction sites, the model may be refined by testing in one centimeter increments around selected sites of the 10-20 system.

These predicted "best fit" locations may then be tested against the two "standard" locations most commonly presented in the current literature (C3-C4 and Cz'-FPz of the 10-20 system) (see Deletis, 2002 and MacDonald et al. 2003, citations below and incorporated by reference). This 3-D effort provides an advantageously sophisticated model, although verification and human testing may still be used, as well.

In a further embodiment, the technique includes adding CT scans to MRI images, and/or applying the model to spinal surgery patients. MRI is effective at imaging soft tissue, but is less effective at imaging bones, because MRI is effective at imaging water molecules within the target tissues. The bony skull is the highest resistivity tissue in the head and a significant barrier for electric current passing into the brain. Our modeling has compensated for this by assuming that dark regions between the brain and the scalp are bony structures. This has the advantage of requiring a single scan of a patient, as long as the quality remains high. Alternatively, MRI images may be collected in three axes (axial, coronal, and sagital), and CT images may be scanned and retroactively adjusted to match the three axes of the MRI scans. The two sets of images may then be digitally co-registered and combined as described above.

Direct Measurement

Currents may be directly measured in the cerebral ventricle of patients who are about to have a ventricular drain placed in their brain for elective shunt placement for hydrocephalus. In this clinical procedure, a small craniotomy is performed, the dura is then opened, and one end of a silastic tube is placed through the brain and into the ventricle for the purpose of draining excess cerebrospinal fluid. This sylastic tube is filled with saline or cerebrospinal fluid to avoid bubbles and used as a drain. Thus, a saline filled tube can act as a recording electrode placed in the ventricle and passing through brain tissues. Record from this tube may be performed by inserting a platinum/iridium probe in the distal end of the tube and connecting the probe to a recording oscilloscope. After the oscilloscope is turned on, three sets of transcranial pulses will be applied to the patient and the pulsed current measured from the ventricular space will be measured. To reach the ventricle, the tube is placed through a section of prefrontal cortex and readings are taken in this region as well. The readings for the current levels in the sampled regions may be compared to the current levels predicted by the GETs model. The sylastic ventricular drain tube itself has resistivity and capacitance properties and these may be determined and tested by placing the tube in a saline filled beaker and testing the resistivity and capacitance of the tube before it is placed in the subject's brain or added to the model.

Biological Assay

In some embodiments, a biological assay is performed to test stimulation of the motor cortex in patients who are having elective spinal surgeries that require tcMEPs as part of their surgical monitoring procedure. Effective current levels for stimulation in clinical patients may be established in this way. Since there is variation in the fine detail location of the motor cortex between individuals, it is advantageous to determine with precision the location of the target muscle as represented in the cortex.

Motor cortex localization may be determined by functional MRI (fMRI). The fMRI may be performed with the subject instructed to move his or her thumb (the abductor pollicis brevis muscle) to obtain precision location information of that muscle's representation in the motor cortex while the fMRI is being performed. The resulting imaged location can then be the target location for modeling of stimulation. The subject's MRI (and/or CT) image is segmented as described. The subject's data are then received for GETs modeling for stimulation.

Stimulation Site Selection

The best location for stimulating electrodes for targeting an identified motor cortex may be selected by the following method. First, the target site is identified. The computer may be programmed to systematically select and test for current density at the target site for each of the locations of the traditional 10-20 system for electrode placements on the head as current injection and extraction sites. In addition to the traditional 10-20 system sites, the eye lids, auditory canals and the nasal passage are typically added, as they represent relevant avenues for bypassing the high resistivity of the skull. After the computer has grossly identified a pair of stimulation and extraction sites, the model may be refined in one centimeter increments around estimated sites. The computer may iterate moving the stimulation sites until new optimized sites are selected for use. The criteria the computer will use for target site evaluation may be the highest current achieved when a 10 Volt constant current square wave signal is modeled. The selected stimulation model is also examined for potential stray currents. In some embodiments, for safety, the selected stimulation model is eliminated if it is judged to affect an area that might produce side effects. In some embodiments, the electrode sites are identified as a pair (i.e., two electrode sites are identified). In some other embodiments, three or more electrode sites are identified as a set. It should be appreciated that with the method described above, the electrode sites can be selected solely from homogeneous or isotropic tissue properties (e.g., resistivity or conductivity values), without using anisotropic properties. Therefore, the method described above eliminates the need for any anisotropic measurement or a database storing anisotropic property values.

Conversely, one or more target sites may be determined from a given set of electrode sites. First, one or more sets of potential electrode sites are identified either manually or using predefined coordinates, such as the 10-20 system. The computer system may use the electrical property map and the FE method to identify the current path for each set of electrode sites. In some embodiments, the computer system also determines a site within the biological tissue that has the highest current density. In some embodiments, the current density at one or more target sites may be determined from the given set of electrode sites.

Figure 17A:
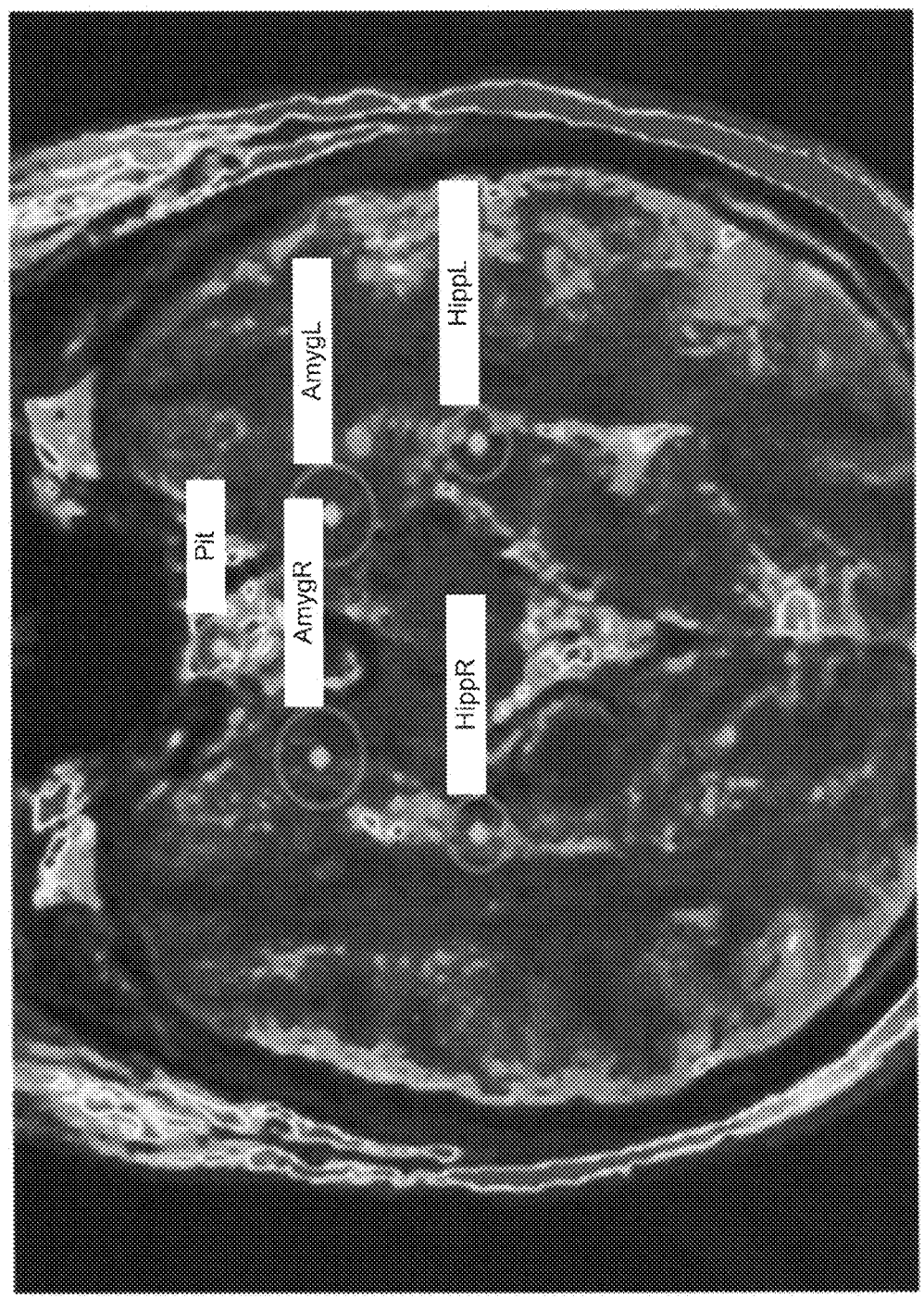

FIGS. 17A and 17B illustrate current densities determined from respective simulations based on MRI images of two individuals in accordance with some embodiments. Each of FIGS. 17A and 17B illustrates current densities in a same brain region simulated for stimulation with 2 mA with the electrodes located at O1 and FPz locations (of the 10-20 system). FIGS. 17A and 17B indicate that the individual illustrated in FIG. 17A would achieve a higher current density at the pituitary gland under the described stimulation condition (e.g., 2 mA at O1-FPz locations) than the individual illustrated in FIG. 17B under the same stimulation condition. Such differences are primarily due to anatomical and physiological differences between the two individuals. Thus, the electrical property map of a respective individual, or the current density map calculated using the electrical property map of the respective individual, can be used to determine whether the respective individual may respond to a particular stimulation condition (e.g., the individual illustrated in FIG. 17B may not respond well to the particular stimulation condition because the current density may be too low). A surgeon may decide not to pursue the electric or magnetic stimulation, or decide to use other electrode locations. In addition, the electrical property map or the current density map of the respective individual may be used to determine whether the particular stimulation condition may be potentially hazardous. For example, a surgeon may decide not to pursue the electric or magnetic stimulation, or decide to use other electrode locations because the current density at certain locations (e.g., amygdala) may be too high. In some embodiments, such decisions may be made automatically by a computer system based on predefined criteria (e.g., a maximum current density threshold and a minimum required current density at a target site) without user input.

tcMEP Recording Conditions

Anesthesia levels, blood pressure, and body temperature is generally kept constant during the tcMEP recording. No muscle relaxants are used for the preferred procedure, except during intubation. The low current levels allow stimuli to be presented through subdermal electrodes. During a patient's surgery, a patient may receive total intravenous anesthesia (TIVA) with propofol and narcotics to negate the inhibiting effect that traditional inhalation agents have on the motor cortex. These procedures are generally several hours long and testing can be done during a stable anesthetic regimen. The motor responses may be recorded from subdermal needle electrodes placed in the target muscle and recorded on a Cadwell Cascade intraoperative monitoring machine. Stimuli may be short duration square wave pulses presented through a constant current stimulator. The exact duration and intensity may be determined by the impedance properties predicted by the modeling.

The stimulus parameters may be identical between groups with a train of 6 square wave 100 μsec pulses with a fixed inter-stimulus interval (ISI) and constant voltage. A minimum voltage and location may be determined by the model or the traditional sites found in the literature. The outcome variable may be the amplitude and duration of response as a reflection of the number of neurons activated in the fMRI identified loci of the motor cortex.

Electrode within or Through the Skull

The skin is a low resistance medium (approximately 230 ohms per cm) and the skull is very high resistance (approximately 1600 ohms per cm). When two or more electrodes are placed on the scalp and electrical energy is passed between them, most of the energy applied passes through the skin and relatively little goes into the brain. Thus the pain that is often felt when electrical current is applied to the head is really the result the electrical current that is passing through pain receptors in the scalp, and not to the stimulus that is reaching the brain. This can tend to limit amounts of electrical stimulus that can be applied to patients for therapy. This shunting of electrical energy though the scalp can be significantly reduced by placing electrodes within or through the skull and insulating the electrode from the scalp. In this manner electrical energy is directed away from the scalp and towards the brain.

Methods of Using the Electrical Property Map

Figure 14:
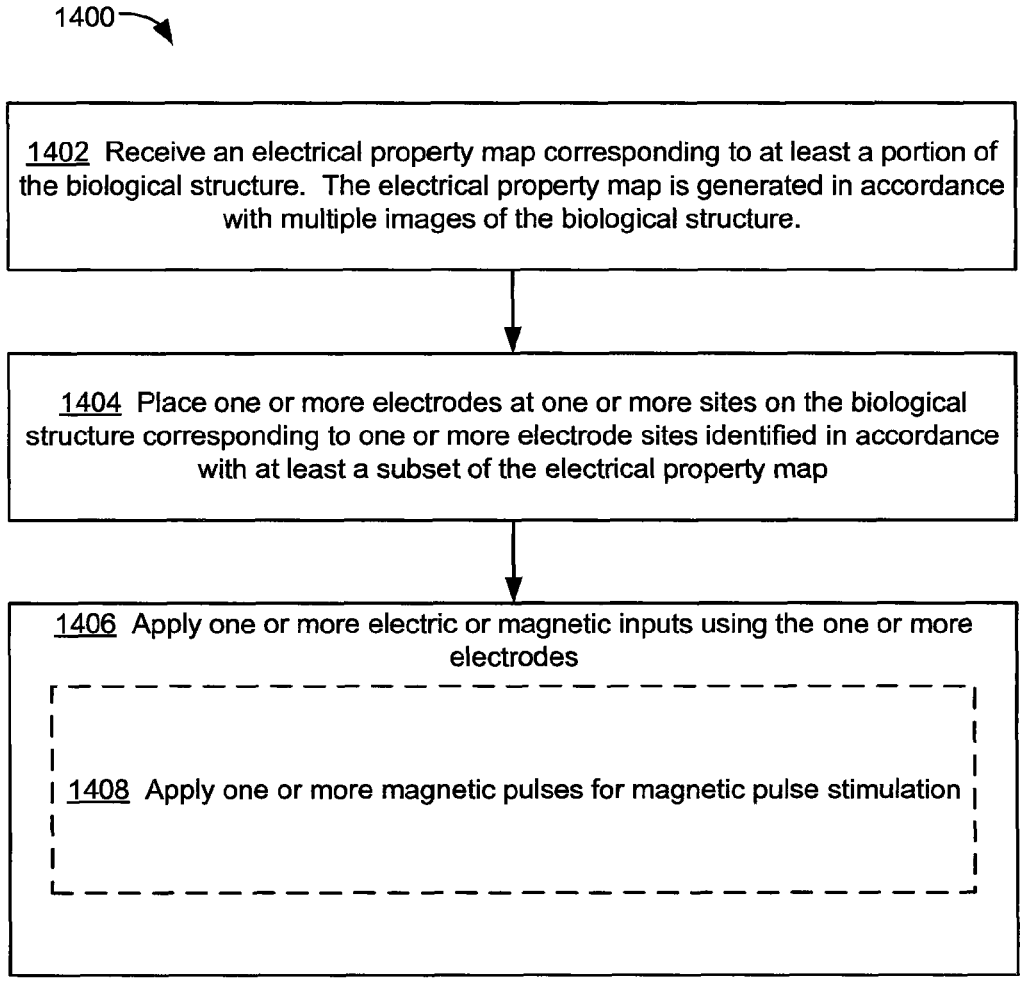
FIG. 14 is a flow diagram illustrating a method for providing electrical or magnetic stimulation of a biological structure in accordance with some embodiments.

FIG. 14 is a flow diagram illustrating a method 1400 for providing electrical or magnetic stimulation of a biological structure in accordance with some embodiments. The method includes (1402) receiving an electrical property map corresponding to at least a portion of the biological structure. The electrical property map is generated in accordance with multiple images of the biological structure (e.g., T1, T2, and PD MRI images of the biological structure, such as brain).

The method includes (1404) placing one or more electrodes at one or more sites on the biological structures corresponding to one or more electrode sites identified in accordance with at least a subset of the electrical property map. In some embodiments, the one or more electrode sites are selected based on one or more simulation results indicating that the current density at a target site (e.g., a portion of the biological structure where application of electrical current is desired) meets a predefined effective current threshold. In some embodiments, the one or more electrode sites are selected based on one or more simulation results indicating that the current density at one or more sites other than the target site does not exceed a predefined safety threshold. For tcMEP monitoring, the one or more electrode sites are located on the scalp (e.g., electrode sites in FIG. 10).

The method includes (1406) applying one or more electric or magnetic inputs using the one or more electrodes (e.g., applying electrical input of a predefined voltage for 100 µs in trains of five pulses). In some embodiments, the method includes monitoring motor evoked potentials in response to the one or more electric or magnetic inputs. In some embodiments, the one or more electric or magnetic inputs (e.g., current and/or voltage) are selected based on one or more simulation results indicating that the current density at the target site meets the predefined effective current threshold. In some embodiments, the one or more electric or magnetic inputs are selected based on one or more simulation results indicating that the current density at one or more sites other than the target site does not exceed a predefined safety threshold.

In some embodiments, the method includes (1408) applying one or more magnetic pulses for magnetic pulse stimulation.

When one or more electrode sites that can more effectively transmit the electrical or magnetic energy to the target site are selected with the electrical property map, a desired level of the current density can be achieved at the target site with electrical currents lower than those used in conventional methods. This is beneficial in many applications. For example, reduced currents may be used to deliver brain stimulation in awake patient populations.

As explained above, electrical property maps can be used for monitoring purposes (e.g., tcMEP monitoring). In some cases, transcranial electrical stimulation may be used in awake patients, as long as discomfort and pain involved are low enough, i.e., when current levels applied across the scalp are low enough as in accordance with some embodiments. For example, the use of the electrical property maps permits reduction of currents to less than 20 mA (at a constant voltage), which may be applied to awake patients for tcMEP monitoring during surgery.

In addition, electrical property maps can be used for therapeutic purposes as well. For example, the reduced currents may be used for treating patients with refractory depression, epilepsy and chronic pain. In some embodiments, such patients may be treated with the electrical current while they are awake, because the applied currents are low.

FIG. 15 is a flow diagram illustrating a method 1500 for killing cells in accordance with some embodiments. The cells typically include pathological cells, such as tumor cells.

The method includes (1502) receiving an electrical property map corresponding to at least a portion of a biological structure. The electrical property map is generated in accordance with multiple images of the biological structure.

The method includes (1504) placing one or more electrodes at one or more sites on the biological structure corresponding to one or more electrode sites identified in accordance with at least a subset of the electrical property map. Although many embodiments are described herein with respect to a brain, it should be noted that the methods and systems described herein are not limited to application to a brain or head region. For example, the one or more electrode sites may be located on any biological structure.

In some embodiments, the method includes (1506) identifying one or more respective locations of the tumor cells in the biological structure; and identifying the one or more electrode sites in accordance with the one or more respective locations of the tumor cells in the biological structure and at least the subset of the electrical property map. For example, the one or more respective locations of the tumor cells may be determined from one or more MRI images (e.g., the multiple MRI images used for generating a combined image), CT scans, and/or by means of other radiological or pathological methods and tools (e.g., ultrasound scans, PET scans, histology, etc.).

The method includes (1508) applying one or more electric inputs using the one or more electrodes for killing the cells in the biological structure. The one or more electric inputs may include an electrical input sufficient to kill the cells. Typically, the cells located in the current patch will be killed or damaged. See Sera et al., which is cited below and incorporated by reference herein, for the use of electricity for killing tumor cells.

Alternatively, the method includes applying one or more electric inputs using the one or more electrodes for arresting proliferation of tumor cells. See Kirson et al., which is cited below and incorporated by reference herein, for the effect of alternating electric fields arresting cell proliferation.

Figure 16:
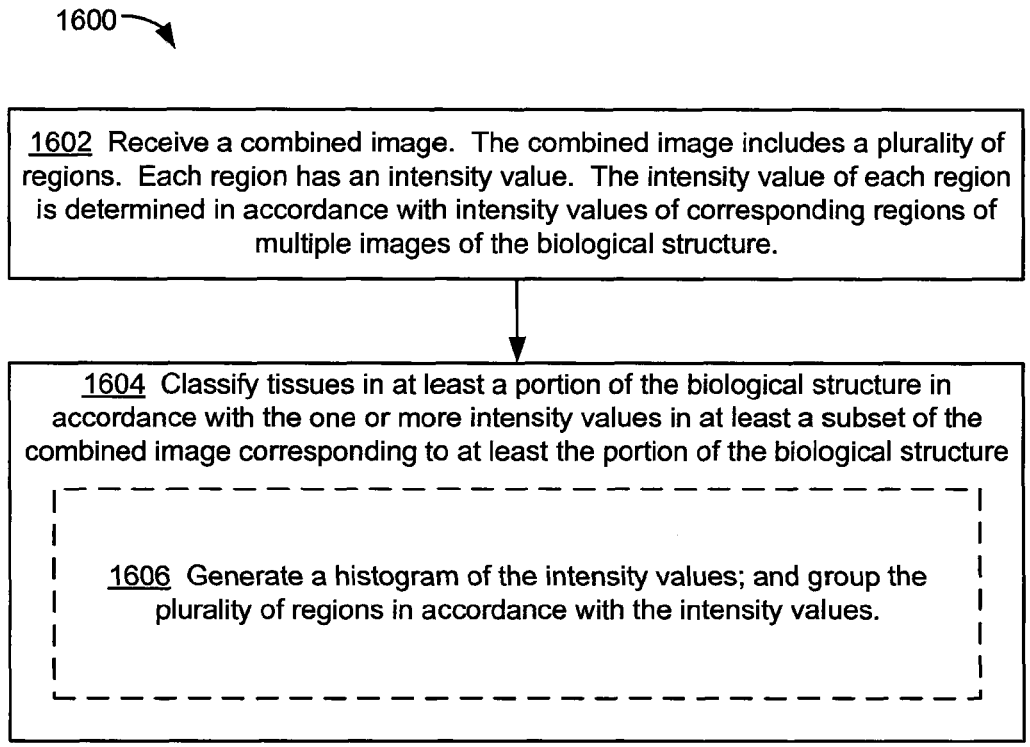
FIG. 16 is a flow diagram illustrating a method for classifying tissues in accordance with some embodiments.

FIG. 16 is a flow diagram illustrating a method 1600 for classifying tissues in accordance with some embodiments. The method 1600 is performed at a computer system having one or more processors and memory storing one or more programs for execution by the one or more processors for performing tissue classification (e.g., the image processing system 1200, FIG. 12). As used herein, the terms "tissue classification" and "classifying tissue" refer to grouping tissues of a similar property together. Tissue classification does not necessarily involve identifying a tissue based on the tissue property. In other words, tissue classification may be used to determine that two separate portions of an image correspond to a same type of tissue, but tissue classification does not necessarily identify the type of tissue (e.g., white matter v. gray matter) that those portions of the image correspond to. However, additional steps (e.g., histology examination) may be followed to identify tissue in each group, thereby correlating the tissue property with a particular group of tissues (e.g., tumor cells).

The computer system receives (1602) a combined image (e.g., the combined image in FIG. 9). The combined image includes a plurality of regions, and each region has an intensity value. The intensity value of each region is determined in accordance with intensity values of corresponding regions of multiple images of the biological structure.

The computer system classifies (1604) tissues in at least a portion of the biological structure in accordance with the one or more intensity values in at least a subset of the combined image corresponding to at least the portion of the biological structure. For example, the computer system groups the tissues shown in the combined image of FIG. 9 based on the intensity values.

In some embodiments, the computer system generates (1606) a histogram of the intensity values, and grouping the plurality of regions in accordance with the intensity values. For example, FIG. 9 shows that each group of regions is represented as one or more respective peaks in the histogram.

The present invention is not limited to the embodiments described above herein, which may be amended or modified without departing from the scope of the present invention, which is as set forth in the appended claims and structural and functional equivalents thereof.

For example, the electrical property map may be used for guiding migration of stem cells. See Zhang et al., which is cited below and incorporated by reference herein, for the general method of guiding migration of stem cells. The electrical property map, and the methods of identifying the electrode sites and/or target sites can be used to generate an electric field within the biological structure to better guide the migration of stem cells.

In methods that may be performed according to embodiments herein and that may have been described above and/or claimed below, the operations have been described in selected typographical sequences. However, the sequences have been selected and so ordered for typographical convenience and are not intended to imply any particular order for performing the operations.

In addition, all references cited above and below herein, in addition to the background and summary of the invention sections, are hereby incorporated by reference into the detailed description of the preferred embodiments as disclosing alternative embodiments and components. The following are incorporated by reference:

Amassian V E. Animal and human motor system neurophysiology related to intraoperative monitoring. In: Deletis V, Shels J, editors. Neurophysiology in Neurosurgery. Amsterdam: Academic Press, 2002:3-23;

Ary J P, Klein S A, Fender D H. Location of sources of evoked scalp potentials: corrections for skull and scalp thicknesses. IEEE Trans Biomed Eng 1981:28; 447-452;

Benar C G, Gotman J. Modeling of post-surgical brain and skull defects in the EEG inverse problem with the boundary element model. Clin Neurophysiol 2002; 113:48-56;

Ben-David, B., Haller G., Taylor P. Anterior spinal fusion complicated by paraplegia. A case report of false-negative somatosensory-evoked potential. Spine 1987, 12:536-9;

Berry M M, Standring S M, Bannister L H. Nervous system. In: Bannister L H, Berry M M, Collins P, Dyson M, Dussek J E, Ferguson M W J, editors. Gray's anatomy. The anatomical basis of medicine and surgery. New York: Churchill Livingstone, 1995:1191;

Bose B, Sestokas A K, Swartz D M. Neurophysiological monitoring of spinal cord function during instrumented anterior cervical fusion. Spine J 2004; 4:202-207;

Calachie B, Harris W, Brindle, F, Green B A, Landy H J. Threshold-level repetitive transcranial electrical stimulation for intraoperative monitoring of central motor conduction. J Neurosurg 2001; 95:161-168;

Chappa, K H Transcranial motor evoked potentials. Electromyogr. Clin. Neurophysiol. 1994; m34:15-21;

Cheney P D, Fetz E E, Palmer S S. Patterns of facilitation and suppression of antagonist forelimb muscles from motor cortex sites in the awake monkey. J Neurophysiol 985; 53:805-820;

Comsol A B, FEMLAB User's Guide v. 3.0. Burlington, Mass.: Comsol, Inc, 2004;

Deletis V. Intraoperative neurophysiology and methodologies used to monitor the functional integrity of the motor system. In: Deletis V, Shels J, editors. Neurophysiology in Neurosurgery. Amsterdam: Academic Press, 2002: 25-51;

Eroglu, A., Solak, M., Ozem, I., and Aynaci, O. Stress hormones during the wake-up test in scoliosis surgery. J. Clin. Anesthesia 2003, 15: 15-18;

Ferree T C, Eriksen K J, Tucker D M. Regional head tissue conductivity estimation for improved EEG analysis. IEEE Trans Biomed Eng 2000; 47; 1584-1592;

Geddes L A, Baker L E. The specific resistance of biological material—a compendium of data for the biomedical engineer and physiologist. Med Biol Eng 1967; 271-293;

Ginsburge H. H., Shetter, A. G., Raudzens, P. A., Postoperative paraplegia with preserved intraopertive somatosensory evoked potentials. J. Neurosurg. 1985; 63:296-300;

Goncalves S I, de Munck J C, Verbunt J P A, Bijma F, Heethaar R M, da Silva F H. In vivo measurement of the brain and skull resistivities using an EIT-based method and realistic models for the head. IEEE Trans Biomed Eng 2003; 50:754-767;

Grimnes S. Martinsen O. G. Bioimpedance and Bioelectricity Basics Academic Press, San Diego, 2000;

Haghighi S S, Zhange R. Activation of the external anal and urethral sphincter muscles by repetitive transcranial cortical stimulation during spine surgery. J Clin Monit Comput 2004; 18:1-5;

Haueisen J, Ramon C. Influence of tissue resistivities on neuromagnetic fields and electric potentials studied with a finite element model of the head. IEEE Trans Biomed Eng 1997; 44:727-735;

Henderson C J, Butler S R, Glass A. The localization of the equivalent dipoles of EEG sources by the application of electric field theory. Electroencephalogr Clin Neurophysiol 975; 39:117-130;

Kavanagh R N, Darcey T M, Lehmann D, Fender D H. Evaluation of methods for the three-dimensional localization of electrical sources in the human brain. IEEE Trans Biomed Eng 1978; 25:421-429;

Kirson E D, Dbalý V, Tovarys F, Vymazal J, Soustiel J F, Itzhaki A, Mordechovich D, Steinberg-Shapira S, Gurvich Z, Schneiderman R, Wasserman Y, Salzberg M, Ryffel B, Goldsher D, Dekel E, Palti Y. Alternating electric fields arrest cell proliferation in animal tumor models and human brain tumors. Proc Natl Acad Sci USA. 2007 Jun. 12; 104(24):10152-7;

Knudsen, V Verification and use of a numerical computer program for simulation in bioimpedance. MSc thesis Dept. of Physics. Univ. Oslo, Norway;

Law S K. Thickness and resistivity variations over the upper surface of the human skull. Brain Topogr 1993; 6:99-109;

Lesser, R. P., Raudzens, P., Luders, H., Nuwer, M. R., et al. Postoperative neurological deficits may occur despite unchanged intraoperative somatosensory evoked potentials. Ann. Neurol. 1986. 19:22-25;

Liu E H, Wong H K, Chia C P, Lim H J, Chen Z Y, Lee T L. Effects of isoflurane and propofol on cortical somatosensory evoked potentials during comparable depth of anaesthesia as guided by bispectral index. Br J Anaesth (in press);

MacDonald D B, Zayed Z A, Khoudeir I, Stigsby B. Monitoring scoliosis surgery with combined multiple pulse transcranial electric motor and cortical somatosensory-evoked potentials from the lower and upper extremities. Spine 2003; 28:194-203;

Mustain W. D. Kendig, R. I., Dissociation of neurogenic motor and somatosensory evoked potentials. A case report Spine. 1991; 16:851-3;

Nadeem M. Computation of electric and magnetic stimulation in human head using the 3-D impedance method. IEEE Trans Biomed Eng 2003; 50:900-907;

Nowinski W L, Bryan R N, Raghavan R. The electronic brain atlas. Multiplanar navigation of the human brain. New York: Thieme, 1997;

Oostendorp T F, Delbeke J, Stegeman D F. The conductivity of the human skull: results of in vivo and in vitro measurements. IEEE Trans Biomed Eng 2000; 47:1487-92;

Pelosi L, Lamb J, Grevitt M, Mehdian S M, Webb J K, Blumhardt L D. Combined monitoring of motor and somatosensory evoked potentials in orthopaedic spinal surgery. Clin Neurophysiol 2002; 113:1082-1091;

Rush S, Driscoll D A. Current distribution in the brain from surface electrodes. Anesth Analgesia 47; 717-723, 1968;

Schneider M. Effect of inhomogeneities on surface signals coming from a cerebral dipole source. IEEE Trans Biomed Eng 1974; 21:52-54;

Sersa G, Kranjc S, Scancar J, Krzan M, Cemazar M. Electrochemotherapy of mouse sarcoma tumors using electric pulse trains with repetition frequencies of 1 Hz and 5 kHz. J Membr Biol. 2010 July; 236(1):155-62;

Ubags L H, Kalkman C J, Been H D, Drummond J C. The use of a circumferential cathode improves amplitude of intraoperative electrical transcranial myogenic motor evoked responses. Anesth Analg 1996; 82:1011-1014;

Vauzelle, C., Stagnara, P., Jouvinroux, P. Functional monitoring of spinal cord activity during spinal surgery. Clin. Orthop. 1973; 93:173-8;

Zentner J. Non-invasive motor evoked potential monitoring during neurosurgical operations on the spinal cord. Neurosurg 1989; 24:709-712;

Zhang J, Calafiore M, Zeng Q, Zhang X, Huang Y, Li R A, Deng W, Zhao M. Electrically Guiding Migration of Human Induced Pluripotent Stem Cells. Stem Cell Rev. 2011 Mar. 5; and US published patent applications nos. 2005/0244036, 2004/0215162, 2004/0102828 and 2002/0156372; and U.S. Pat. Nos. 6,608,628, 6,763,140, 5,750,895, 5,805,267, 6,106,466, 6,236,738, 6,476,804, 6,959,215, 6,330,446, 7,010,351, 6,463,317, 6,322,549, 6,248,080, 6,230,049, 6,006,124, 6,045,532, 6,916,294, 6,937,905, 6,675,048, 6,607,500, 6,560,487, 6,324,433, 6,175,769, 5,964,794, 5,725,377, 5,255,692, 4,611,597, 4,421,115, and 4,306,564.

What is claimed is:

1. A method performed by a computer system having one or more processors and memory storing one or more programs for execution by the one or more processors, the method comprising:

accessing multiple images of a biological structure, wherein the multiple images of the biological structure include one or more of: a T1 MRI image, a T2 MRI image, and a proton density MRI image;

generating a combined image based on the multiple images of the biological structure, said combined image having a plurality of elements each corresponding to a respective pixel or voxel in the T1 MRI image, T2 MRI image, and proton density MRI image;

calculating electrical property values from pixel or voxel data of said combined image, the respective electrical property values comprising respective tissue resistivity values, wherein determining the respective electrical property values includes determining respective tissue resistivity values in accordance with an equation:

$$R(v)=K(1-v)^E+D,$$

where R is a respective tissue resistivity value, K is a multiplier value, v is a respective normalized numeric value representing an intensity of a respective pixel or voxel of the combined image, E is an exponent, and D is a tissue density value;

generating an electrical property map of the calculated electrical property values for the biological structure; and displaying the electrical property map on a display device of the computer system.

2. The method of claim 1, wherein said respective pixel or voxel each has an intensity value represented with multiple data bits; and generating the combined image includes, for each pixel or voxel, interleaving at least a subset of the multiple data bits from respective images.

3. The method of claim 1, wherein said electrical property values further include conductivity values.

4. The method of claim 1 wherein generating the combined image includes generating a weighted-sum image of the multiple images based on the intensities of the respective pixels or voxels in the multiple images.

5. The method of claim 1, wherein:
the multiple images include a functional MRI image; and
the method includes:
overlaying at least a subset of the functional MRI image onto the electrical property map of the biological structure.

6. The method of claim 1, further comprising:
identifying one or more electrode sites for providing stimulation of at least a respective region of biological tissue of the biological structure in accordance with at least a subset of the electrical property map.

7. The method of claim 1, further comprising:
identifying one or more inductance sites for providing magnetic pulse stimulation of at least a respective region of biological tissue of the biological structure in accordance with at least a subset of the electrical property map.

8. The method of claim 1, wherein the electrical property values are isotropic.

9. The method of claim 1, wherein the biological structure includes brain tissue, and the method further comprises:
identifying one or more electrode sites for providing transcranial electrical stimulation of at least a respective region of the biological tissue in accordance with at least the subset of the electrical property map.

10. The method of claim 1, wherein generating the electrical property map further comprises:
accessing one or more diffusion-weighted MRI images from the multiple images of the biological structure; and determining a plurality of anisotropic electrical property values from the one or more diffusion-weighted MRI images.

11. The method of claim 10, further comprising adjusting the generated electrical property map according to the plurality of anisotropic electrical property values.

12. The method of claim 10, further comprising determining the plurality of anisotropic electrical property values by analyzing the one or more diffusion-weighted MRI images of the biological structure using a diffusion tensor analysis method.

13. The method of claim 10, further comprising determining the plurality of anisotropic electrical property values by analyzing the one or more diffusion-weighted MRI images of the biological structure using a Q-ball analysis method.

14. A method performed by a computer system having one or more processors and memory storing one or more programs for execution by the one or more processors, the method comprising:
   accessing multiple images of a biological structure;
   generating an electrical property map of at least a portion of the biological structure in accordance with two or more of the multiple images including:
      generating a combined image of at least the portion of the biological structure using the two or more of the multiple images; and
      determining respective electrical property values of the electrical property map for respective regions of the combined image, wherein the respective electrical property values include respective tissue resistivity values; and determining the respective electrical property values includes determining respective tissue resistivity values in accordance with an equation:

$$R(v)=K(1-v)^E+D,$$

where R is a respective tissue resistivity value, K is a multiplier value, v is a respective normalized numeric value representing an intensity of a respective pixel or voxel of the combined image, E is an exponent, and D is a tissue density value; and
   displaying the electrical property map on a display device of the computer system.

15. The method of claim 14, wherein the biological structure includes brain tissue, and the method further comprises:
   identifying one or more electrode sites for providing transcranial electrical stimulation of at least a respective region of the biological tissue in accordance with at least the subset of the electrical property map.

16. The method of claim 14, wherein generating the electrical property map further comprises:
   accessing one or more diffusion-weighted MRI images from the multiple images of the biological structure; and
   determining a plurality of anisotropic electrical property values from the one or more diffusion-weighted MRI images.

17. The method of claim 16, further comprising adjusting the generated electrical property map according to the plurality of anisotropic electrical property values.

18. The method of claim 16, further comprising determining the plurality of anisotropic electrical property values by analyzing the one or more diffusion-weighted MRI images of the biological structure using a diffusion tensor analysis method.

19. The method of claim 14, wherein the multiple images of the biological structure includes one or more of: a T1 MRI image, a T2 MRI image, a proton density MRI image, a magnetic resonance angiography image, and an X-ray computed-tomography image, and wherein the combined image further includes a plurality of elements each corresponding to a respective pixel or voxel in the T1 MRI image, T2 MRI image, proton density MRI image, magnetic resonance angiography image, and the X-ray computed-tomography image.

20. A non-transitory computer readable storage medium, storing one or more programs for execution by one or more processors of a computer system, the one or more programs including instructions for:
   accessing multiple images of a biological structure, wherein the multiple images of the biological structure include one or more of: a T1 MRI image, a T2 MRI image, and a proton density MRI image;
   generating a combined image based on the multiple images of the biological structure, said combined image having a plurality of elements each corresponding to a respective pixel or voxel in the T1 MRI image, T2 MRI image, and proton density MRI image;
   calculating electrical property values from pixel or voxel data of said combined image, the respective electrical property values comprising respective tissue resistivity values, wherein determining the respective electrical property values includes determining respective tissue resistivity values in accordance with an equation:

$$R(v)=K(1-v)^E+D,$$

where R is a respective tissue resistivity value, K is a multiplier value, v is a respective normalized numeric value representing an intensity of a respective pixel or voxel of the combined image, E is an exponent, and D is a tissue density value;
   generating an electrical property map of the calculated electrical property values for the biological structure; and
   displaying the electrical property map on a display device of the computer system.

* * * * *